(12) United States Patent
Allen et al.

(10) Patent No.: US 10,688,067 B2
(45) Date of Patent: Jun. 23, 2020

(54) STERILIZED CHLORHEXIDINE ARTICLE AND METHOD OF STERILIZING A CHLORHEXIDINE ARTICLE

(71) Applicant: Sage Products, LLC, Cary, IL (US)

(72) Inventors: Jennifer M. Allen, Lakewood, IL (US); Christopher J. Grannis, Algonquin, IL (US); Syed M. Hasan, Cary, IL (US); Timothy P. Manthei, Kenosha, IL (US); Niles R. Manwill, Crystal Lake, IL (US)

(73) Assignee: Sage Products, LLC, Cary, IL (US)

( * ) Notice: Subject to any disclaimer, the term of this patent is extended or adjusted under 35 U.S.C. 154(b) by 0 days.

(21) Appl. No.: 16/557,160

(22) Filed: Aug. 30, 2019

(65) Prior Publication Data

US 2019/0388368 A1 Dec. 26, 2019

Related U.S. Application Data

(63) Continuation of application No. 16/231,034, filed on Dec. 21, 2018, now Pat. No. 10,398,642, which is a continuation of application No. 15/360,037, filed on Nov. 23, 2016, now Pat. No. 10,188,598.

(60) Provisional application No. 62/259,727, filed on Nov. 25, 2015.

(51) Int. Cl.
*A61K 31/155* (2006.01)
*A61K 9/00* (2006.01)

(52) U.S. Cl.
CPC .......... *A61K 31/155* (2013.01); *A61K 9/0014* (2013.01)

(58) Field of Classification Search
CPC ........ A01N 47/44; A01N 31/02; A01N 25/02; A01N 43/40; A01N 2300/00; A01N 25/00; A01N 61/00; A01N 25/34; A01N 25/08; A01N 33/12; A01N 55/02; A01N 25/04; A61K 31/155; A61K 31/14; A61K 31/045; A61K 31/22; A61K 2300/00; A61K 33/38; A61K 47/10; A61K 31/085; A61K 31/185; A61K 31/191; A61K 31/194; A61K 31/685; A61K 31/785; A61K 45/06; A61K 47/183; A61K 47/186; A61K 9/0014; A61K 9/0019; A61K 31/00; A61K 31/205; A61K 47/34; A61K 8/0208; A61K 8/345; A61K 8/43; A61K 9/06; A61K 9/122; A61L 26/0023; A61L 2300/404; A61L 2/0023; A61L 2/28; A61L 26/0014; A61L 2/04; A61L 26/0052; A61L 27/34; A61L 27/54; A61L 2/087; A61L 2202/21; A61L 2300/402; A61L 2300/414; A61L 2/081; A61L 15/32; A61L 15/38; A61L 15/40; A61L 15/46; A61L 2202/181; A61L 2300/204; A61L 2300/236; A61L 2300/252; A61L 2300/254; A61L 2300/606; A61L 2300/61; A61L 2300/802; A61L 24/0015; A61L 24/0021; A61L 24/0031; A61L 27/3604; A61L 27/3683; A61L 27/50; A61L 27/56; A61L 2/0035; A61L 2/082; A61L 2/18; A61L 15/28; A61L 15/42; A61L 15/425; A61L 15/44; A61L 15/62; A61L 2202/22; A61L 2202/24; A61L 2202/26; A61L 2300/222; A61L 2300/406; A61L 2300/602; A61L 2300/62; A61L 2/0005; A61L 2/0011; A61L 2/007; A61L 2/0088; A61L 2/08; A61L 2/232; A61L 2/24; A61L 2/26
See application file for complete search history.

(56) References Cited

U.S. PATENT DOCUMENTS

| | | |
|---|---|---|
| 5,334,388 A | 8/1994 | Hoang et al. |
| 5,383,505 A | 1/1995 | Cordasco, Jr. |
| 5,441,741 A | 8/1995 | Cheong |
| 5,776,430 A | 7/1998 | Osborne et al. |
| 6,383,505 B1 | 5/2002 | Kaiser et al. |
| 6,429,444 B1 | 8/2002 | Korenev et al. |
| 6,914,253 B2 | 7/2005 | Korenev et al. |
| 7,427,574 B2 | 9/2008 | Allen |
| 8,221,365 B2 | 7/2012 | Keaty et al. |
| 8,986,608 B2 | 3/2015 | Lam et al. |
| 9,078,934 B1 | 7/2015 | Degala et al. |
| 2004/0050737 A1 | 3/2004 | Burton et al. |
| 2004/0191274 A1 | 9/2004 | Grayson et al. |
| 2004/0241214 A1 | 12/2004 | Kirkwood et al. |
| 2005/0040339 A1 | 2/2005 | Deady Garcia et al. |
| 2006/0079143 A1 | 4/2006 | Phan et al. |
| 2007/0135006 A1 | 6/2007 | Michaels et al. |
| 2007/0148215 A1 | 6/2007 | Teslenko et al. |
| 2010/0166599 A1 | 7/2010 | Kowalski |
| 2012/0053322 A1 | 3/2012 | Owens et al. |
| 2012/0197415 A1 | 8/2012 | Montanari et al. |
| 2014/0215969 A1 | 8/2014 | Parthun et al. |

(Continued)

FOREIGN PATENT DOCUMENTS

| | | |
|---|---|---|
| CN | 104434652 A | 3/2015 |
| EP | 0 653 70 A1 | 11/1982 |

(Continued)

OTHER PUBLICATIONS

CN104434652A translation (Year:2015).

(Continued)

*Primary Examiner* — Audrea B Coniglio
(74) *Attorney, Agent, or Firm* — Foley & Lardner LLP

(57) ABSTRACT

The present disclosure provides a sterilized chlorhexidine product for topical disinfection. The product includes a sterilized chlorhexidine gluconate composition, an applicator for facilitating application of the sterilized chlorhexidine composition, and a barrier configured to be compromised to impregnate the applicator with the sterilized chlorhexidine gluconate composition. The sterilized chlorhexidine gluconate composition includes chlorhexidine gluconate and alcohol.

19 Claims, 5 Drawing Sheets

(56) References Cited

U.S. PATENT DOCUMENTS

| | | | |
|---|---|---|---|
| 2014/0322072 A1 | 10/2014 | Margoosian et al. | |
| 2015/0190535 A1 | 7/2015 | Degala et al. | |
| 2015/0190536 A1 | 7/2015 | Degala et al. | |
| 2015/0209187 A1 | 7/2015 | Gutierrez et al. | |
| 2015/0231248 A1 | 8/2015 | Scholz | |
| 2015/0297764 A1 | 10/2015 | Degala et al. | |

FOREIGN PATENT DOCUMENTS

| | | |
|---|---|---|
| EP | 0 356 264 A2 | 2/1990 |
| GB | 1 161 528 A | 8/1969 |
| JP | 2014-062060 A | 4/2014 |

OTHER PUBLICATIONS

Denton, Graham, "Chlorhexidine", In: Block, S., editor. Disinfection, Sterilization and Preservation, 5th Edition. Philadelphia: Lippincott, Williams & Wilkins, 2001, 321-336.

English language abstract and machine-assisted translation for JP2014062060 extracted from espacenet.com Oct. 16, 2017; 9 pages.

Kelly M. Pyrek, "Sterility of Antiseptic Products: FDA Investigates, Deliberates on Potential Recommendations", Infection Control Today, Jul. 2013: 24-26.

Toru Yamaguchi, "Electron Beam Sterilization for Drug Products Using Freezing Irradiation" J_ Antibact. Antifung. Agents vol. 41, No. 10, pp. 535-544 (2013).

Toru Yamaguhi, Electron Beam Sterilization of Chlorhexidine Gluconate/Ethanol Disinfectant, J_ Antibacterial and Antifungal Agents, Japan, vol. 41, No. 9, pp. 469-474 (2013).

U.S. Department of Health and Human Services et al., Guidance for Industry: Sterile Drug Products Produced by Aseptic Processing—Current Good Manufacturing Practice, dated Sep. 2004, 63 pages.

Vigeant, Patrice et al., "An Outbreak of Serratia marcescens Infections Related to Contaminated Chlorhexidine", Concise Communications, Infection Control and Hospital Epidemiology, Oct. 1998, vol. 19, No. 10; pp. 791-794.

Weber, David J_ et al., "Outbreaks Associated with Contaminated Antiseptics and Disinfectants", Antimicrobial Agent and Chemotherapy, Dec. 2007 vol. 51 No. 12, pp. 4217-4224.

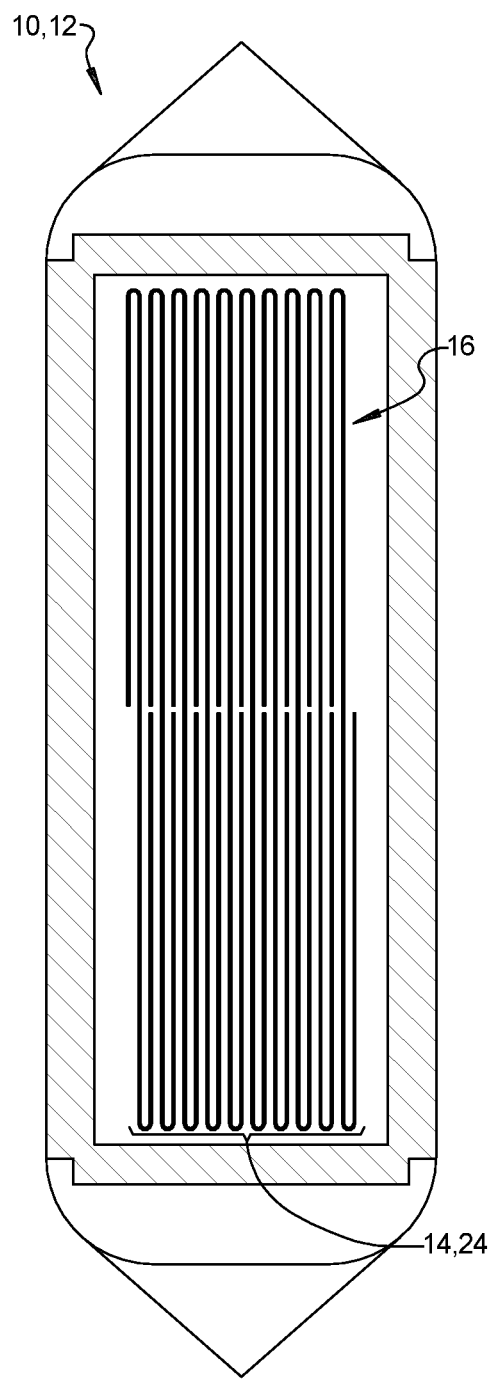 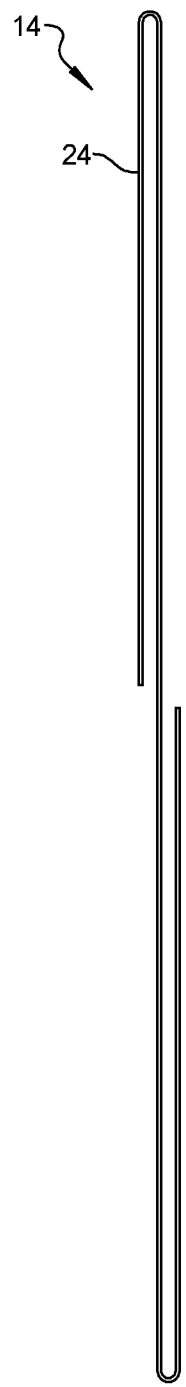
FIG. 3
FIG. 4

STERILIZED CHLORHEXIDINE ARTICLE AND METHOD OF STERILIZING A CHLORHEXIDINE ARTICLE

CROSS-REFERENCE TO RELATED APPLICATIONS

This application is a continuation of U.S. patent application Ser. No. 16/231,034, filed on Dec. 21, 2018, which is a continuation of U.S. patent application Ser. No. 15/360,037, filed on Nov. 23, 2016, which claims priority to and the benefit of U.S. Patent Application No. 62/259,727, filed on Nov. 25, 2015. The entire contents of each are hereby incorporated by reference.

BACKGROUND

The embodiments described herein relate to a sterilized chlorhexidine article and a method of sterilizing a chlorhexidine article.

Healthcare-associated infections (HAI's), which are infections contracted during the course of treatment for a medical or surgical condition, are a significant problem worldwide. HAI's are often caused by pathogenic microorganisms colonizing the patient's skin, mucous membranes, or hollow viscera. Surgery, trauma, and indwelling devices cause a breach in the body's natural barriers thereby providing a pathway for such pathogens to colonize and infect normally sterile areas of the body.

Measures to reduce colonization with pathogens have proven effective in reducing HAI's. One measure to reduce pathogens on the skin and mucous membranes is the topical application of antiseptics such as chlorhexidine. A convenient and effective means of applying chlorhexidine to the skin or mucous membranes is with the use of an applicator. For example, among their many uses, applicators may be used to apply chlorhexidine to decolonize the skin or mucous membranes of a patient or a healthcare worker prior to a surgical procedure to help prevent a surgical site infection, or they may be used ion hospitalized patients with indwelling devises such as central venous catheters, urinary catheters, or endotracheal tubes to routinely decolonize the patient's skin or mucous membranes to help prevent self-infection.

It has been a challenge to develop a chlorhexidine article, and a method of sterilizing a chlorhexidine article.

SUMMARY

In one embodiment, a sterilized chlorhexidine product is provided. The sterilized chlorhexidine product comprises a package defining an interior volume. The sterilized chlorhexidine product further comprises a sterilized chlorhexidine article. The sterilized chlorhexidine article comprises a sterilized applicator and a sterilized antiseptic composition impregnated in the sterilized applicator. The sterilized antiseptic composition comprises a sterilized solvent. The sterilized antiseptic composition further comprises a sterilized antibacterial agent dissolved in the sterilized solvent. The sterilized applicator and the sterilized antiseptic composition are disposed in the interior volume of the package. The sterilized chlorhexidine article has a Sterility Assurance Level of from $10^{-3}$ to $10^{-9}$.

The present disclosure also provides a method of sterilizing a chlorhexidine article. The method comprises providing an applicator. The method further comprises providing an antiseptic composition comprising a solvent and an antibacterial agent dissolved in the solvent. The method further comprises sealing the chlorhexidine article inside the package to form a chlorhexidine product. The method further comprises cooling the chlorhexidine product. The method further comprises sterilizing the chlorhexidine product to form a sterilized chlorhexidine article.

BRIEF DESCRIPTION OF THE FIGURES

Advantages of the present invention will be readily appreciated as the same becomes better understood by reference to the following detailed description when considered in connection with the accompanying drawings wherein:

FIG. 3 is a cross-sectional view of the sterilized chlorhexidine product of FIG. 1 including a plurality of sterilized chlorhexidine articles.

FIG. 4 is an expanded view of one of the plurality of sterilized chlorhexidine articles of FIG. 3.

DETAILED DESCRIPTION

In one embodiment, as shown in FIGS. 1, 2, 3, and 4, a sterilized chlorhexidine product 10 comprises a package 12 and a chlorhexidine article 14. The package 12 defines an interior volume 16. The chlorhexidine article 14 is removably disposed in the interior volume 16 of the package 12.

Figure 1:
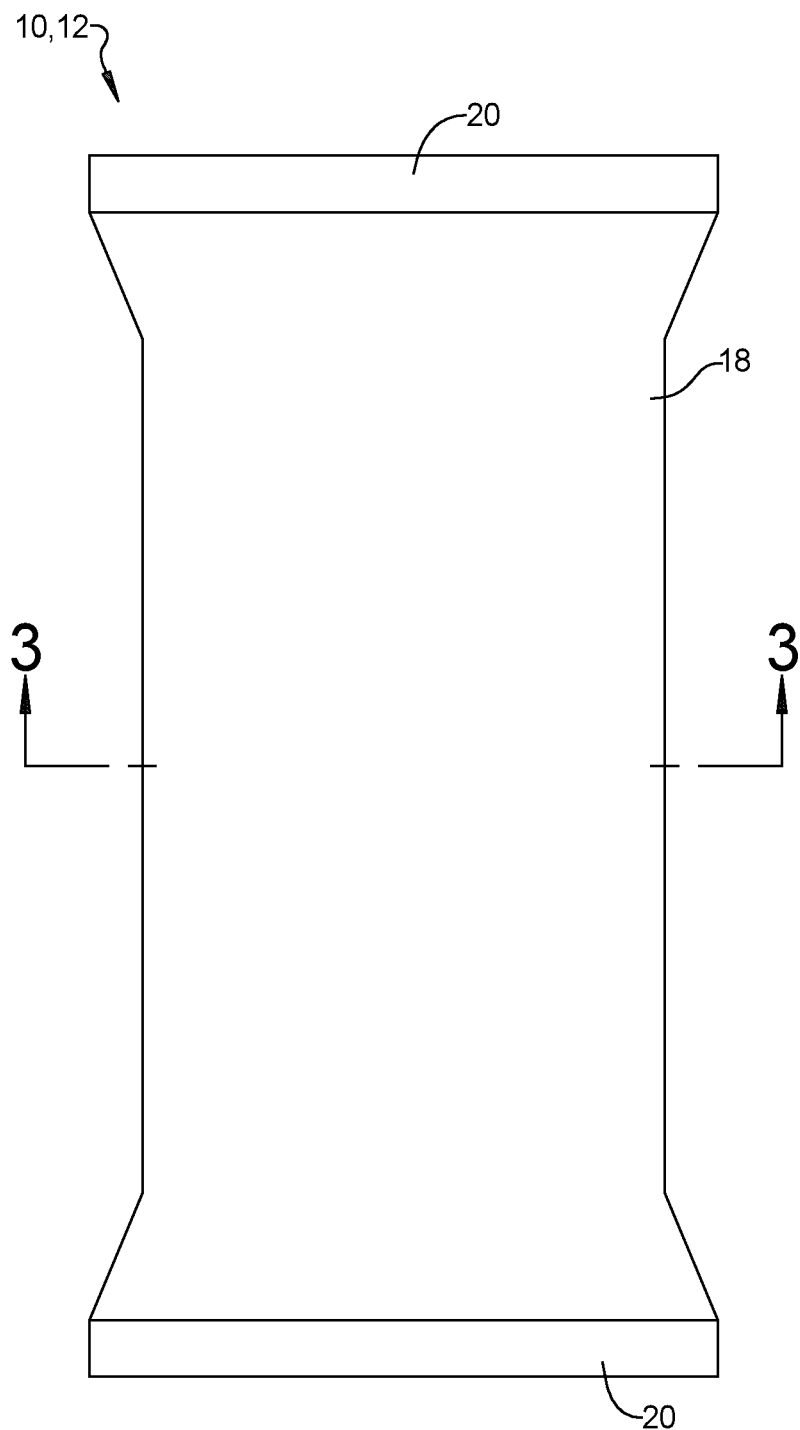
FIG. 1 is a top view of a sterilized chlorhexidine product in accordance with one embodiment.

In some embodiments, the package 12 comprises a film 18 having sealed end portions 20 as shown in FIG. 1. The package 12 may have a rectangular geometry. Of course, it is contemplated the package 12 may have any geometrical configuration suitable for receiving the chlorhexidine article 14 such as, by way of non-limiting example, a rectangular geometry.

Referring to FIGS. 1 and 3, in the illustrated embodiment, the film 18 and the sealed end portions 20 form a hermetic seal about the interior volume 16 and the chlorhexidine articles 14 disposed therein. In this manner, the package 12 protects the chlorhexidine articles 14 from contamination because the chlorhexidine articles 14 are not exposed to the environment outside the package 12. Thus, the package 12 is particularly suitable for terminal sterilization processes such as those described in detail below. While a specific configuration of the package is described, it is contemplated that the package may be adapted based on the configuration of the chlorhexidine articles 14 disposed therein.

In some embodiments, the package may further comprise a tear seal that facilitates access to the chlorhexidine articles disposed in the package. The tear seal may be arranged on the package such that the tear seal does not compromise the hermetic seal formed by the film and the sealed end portions. In this manner, the package may hermetically seal the chlorhexidine articles disposed therein and also allow a patient care provider to easily access the chlorhexidine articles.

In other embodiments, the film may define an outlet for dispensing the chlorhexidine articles disposed within the package. The package may further comprise a label for the outlet. The label may be applied to an external surface of the package over the outlet. The label may have a free or non-adhered end for peeling the label to expose the outlet. Of course, it will be appreciated that when the package comprises an outlet and a label, the package may not hermetically seal the chlorhexidine articles and thus may not be suitable for terminal sterilization processes.

Figure 2:
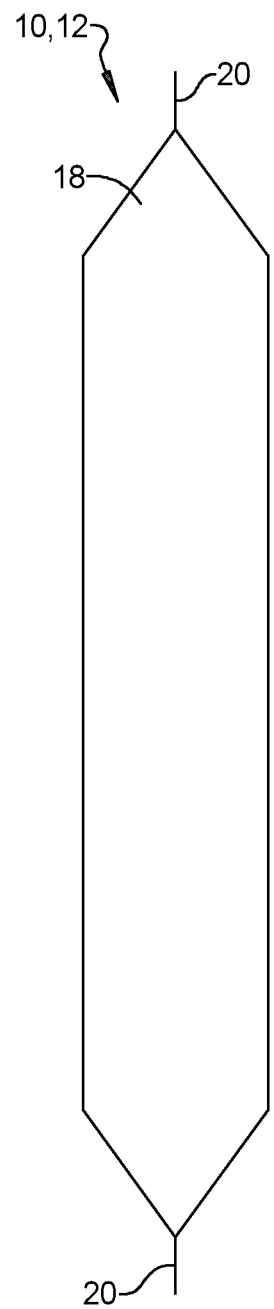
FIG. 2 is a side view of the sterilized chlorhexidine product of FIG. 1.

In certain embodiments, one or more chlorhexidine articles 14 may be disposed in the interior volume 16 of the package 12. The number of chlorhexidine articles 14 disposed into each package 12 is not particularly limited, and may correspond to the desired dosage of antiseptic intended to be delivered to the patient. In other embodiments, a single chlorhexidine article 14 is disposed in the interior volume 16 of the package 12. More particularly, in some embodiments, the number of chlorhexidine articles 14 disposed in the package 12 may be the same as the number of chlorhexidine articles 14 that are used for a particular task. As an example, when the particular task requires six chlorhexidine articles 14, six chlorhexidine articles 14 may be disposed in each package. In this manner, a patient care provider will be discouraged from using either too many, or too few, chlorhexidine articles 14 for the particular task. In other embodiments, the one or more of chlorhexidine articles 14 disposed in the package may be of from 2 to 10, of from 2 to 8, of from 2 to 6, or of from 2 to 4. In one embodiment, two chlorhexidine articles 14 are disposed in each package 12. With reference to FIG. 2, in the illustrated embodiment, ten chlorhexidine articles 14 are disposed in the package 12. Of course, still other quantities of chlorhexidine articles 14 may be disposed in each package 12. It should be appreciated that in other instances, the chlorhexidine articles 14 are not disposed within the interior volume 16 of the package 12, but may be prevented from exposure to the external environment through other means.

Figure 5:
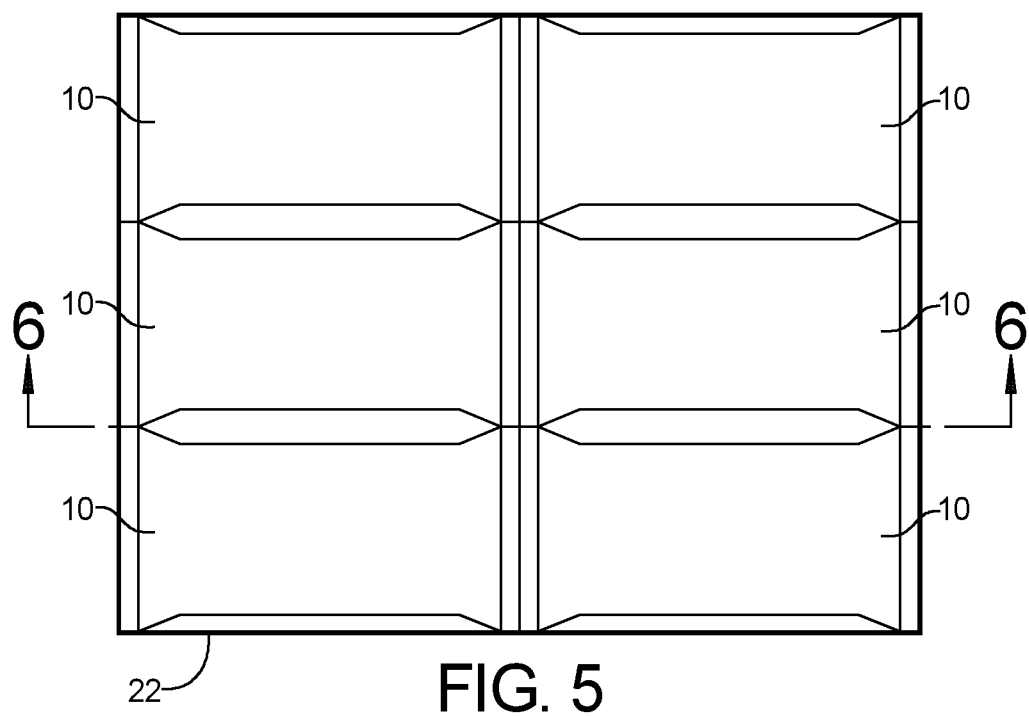
FIG. 5 is a top view of a shipping container containing a plurality of the sterilized chlorhexidine products of FIG. 1.
Figure 6:
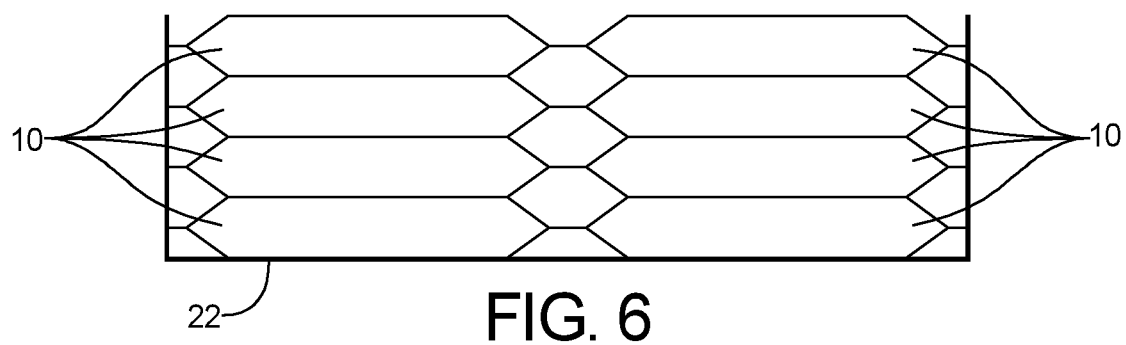
FIG. 6 is a cross-sectional view of the shipping container of FIG. 6.

With reference to FIGS. 5 and 6, in some embodiments, a one or more of chlorhexidine products 10 may be disposed in a shipping container 22, such as a cardboard box 22. The number of chlorhexidine products 10 disposed in the shipping container 22 is advantageously selected based on the type of sterilizing process to be applied. For example, the shipping container may comprise of from 5 to 50 chlorhexidine products 10. In other embodiments, the shipping container 22 may comprise fewer than twenty sterilized chlorhexidine products 10 to permit sterilization of all chlorhexidine articles 14 disposed therein. In still other embodiments, the shipping container may comprise of from 40 to 150 sterilized chlorhexidine products 10. Of course, still other quantities of sterilized chlorhexidine products 10 may be disposed in the shipping container 22.

It should be appreciated that the present disclosure describes a method of sterilizing a chlorhexidine product to form a sterilized chlorhexidine article. As such, throughout this disclosure, description that accompanies the terms the chlorhexidine article, or components and compositions thereof, may be referred to as the 'sterilized' component or composition upon being exposed to suitable processing where such sterility can be validated. By way of non-limiting example, the sterility of the chlorhexidine article may be validated in accordance with ISO 11137.

In certain embodiments, the sterilized chlorhexidine article is intended to be used by a patient care provider for disinfecting skin or mucous membranes of a patient, such as disinfecting skin or mucous membranes of the patient prior to surgery or to routinely disinfect the skin during hospitalization. Alternatively, the sterilized chlorhexidine article may be used to maintain hygiene of a patient, particularly a patient unable to shower or bathe.

With reference to FIG. 4, the chlorhexidine article 14 comprises an applicator 24 and an antiseptic composition. The applicator 24 facilitates topical application of the antiseptic composition to the skin or mucous membranes of a patient. As such, the applicator 24 may take any form suitable for topically applying the antiseptic composition to the skin or mucous membranes of a patient. Characteristics that may be considered when determining whether an applicator 24 is suitable include, by way of non-limiting example, porosity, absorbency, skin or mucous membrane contactable surface area, biocompatibility, ability of the applicator to retain the antiseptic composition, cost of production, etc. By way of non-limiting example, suitable examples of the applicator 24 include a cloth, a foam, a brush, a squirt bottle, a roller, etc.

In certain embodiments, the applicator 24 may be suitable for impregnation with the antiseptic composition such that the antiseptic composition remains dispersed in the applicator until the chlorhexidine article 14 is applied to the skin or mucous membranes of a patient. In this manner, the antiseptic composition of the chlorhexidine article 14 remains impregnated in and retained by the applicator 24 when the chlorhexidine article 14 is disposed within the package 12. When the applicator 24 is applied to the skin or mucous membranes of the patient, the antiseptic composition is transferred from the applicator 24 to the skin or mucous membranes of the patient.

In some embodiments, the applicator may further comprise a receptacle for receiving the antiseptic composition. When the applicator comprises a receptacle, the antiseptic composition may be received in the receptacle. The antiseptic composition received in the receptacle may be subsequently impregnated in the applicator by a patient care provider when the chlorhexidine article is being used to disinfect the skin or mucous membranes of a patient. In this manner, the antiseptic composition does not need to be impregnated in and retained by the applicator prior to disposing the chlorhexidine article in the package. In such embodiments, a barrier may be positioned between the applicator and the receptacle that may be compromised upon activation by the patient care provider.

With reference to FIG. 4, in one embodiment, the applicator 24 may comprise a cloth 24. The cloth 24 may be woven, knitted, non-woven, velour, felt, flocked, needle-punched, tufted, stitch bonded, fusion-bonded, or combinations thereof. Of course, still other types of cloth are contemplated. The cloth 24 may have any weight suitable for applying the antiseptic composition to the skin or mucous membranes of the patient such as, by way of non-limiting example, of from 3.0 to 7.0, of from 4.0 to 6.0, or of from 4.5 to 5.5, ounce per square yard. The cloth 24 may have a tensile strength suitable for applying the antiseptic composition such as, by way of non-limiting example, at least 15, at least 20, or at least 25, pounds per inch in a given direction, with the given direction correlating to a machining direction of the cloth 24. The cloth 24 may have any thickness suitable for applying the antiseptic composition to the skin or mucous membranes of a patient such as, by way of non-limiting example, of from 0.035 to 0.145, of from 0.45 to 0.135, of from 0.055 to 0.125, of from 0.075 to 0.115, or of from 0.085 to 0.105 inches.

In some embodiments, the cloth 24 is disposable. When the cloth 24 is disposable, the cloth 24 may be disposed of after use so as to minimize the chance of contaminating the skin or mucous membranes of a patient during re-use. Of course, in other embodiments, the cloth 24 is re-usable.

The cloth 24 may comprise a first fiber. The first fiber may be a synthetic fiber or a natural fiber. When the first fiber is a synthetic fiber, the first fiber may be selected from the group comprising polyester fiber, polypropylene fiber, polyethylene fiber, rayon fiber, nylon fiber, acrylic fiber, acetate fiber, spandex fiber, latex fiber, Kevlar fiber, or combinations thereof. Of course still other types of synthetic fiber are contemplated such as, by way of non-limiting example, polyamide fiber, azlon fiber, modacrylic fiber, novoloid fiber, nytril fiber, saran fiber, vinal fiber, vinyon fiber, regenerated cellulose fiber, and cellulose acetate fiber. In instances where the first fiber comprises a natural fiber, the first fiber may be selected from the group comprising cotton fiber, wool fiber, silk fiber, jute fiber, and linen fiber. Of course, still other types of natural fiber are contemplated.

In some embodiments, the cloth 24 may comprise a second fiber in addition to the first fiber. The second fiber may comprise any of the materials contemplated for the first fiber. When present, the second fiber may be different from the first fiber or the same as the first fiber. For example, the first fiber may be polyester fiber and the second fiber may be polyester fiber. Alternatively, the first fiber may be polyester fiber and the second fiber may be polypropylene fiber. Of course, still other combinations of the first fiber and second fiber are contemplated. Moreover, it is contemplated that the cloth may comprise three or more fibers comprising any of the materials contemplated for the first fiber.

When present, the second fiber may be different from the first fiber or the same as the first fiber. For example, the first fiber may be polyester fiber and the second fiber may be polyester fiber. Alternatively, the first fiber may be polyester fiber and the second fiber may be polypropylene fiber. Of course, still other combinations of the first fiber and second fiber are contemplated.

In one embodiment, the first fiber has a length of from 1.0 to 3.0 inches. In another embodiment, the first fiber has a length of from 1.0 to 2.0 inches. In other embodiments, the first fiber has a length of from 0.5 to 6.0, of from 0.5 to 5.0, of from 0.5 to 4.0 or from 0.5 to 3.0, inches. In still other embodiments, the first fiber has a length of from 2.0 to 6.0, of from 3.0 to 6.0, of from 4.0 to 6.0, or of from 5.0 to 6.0, inches. In still other embodiments, the first fiber has a length of from 0.5 to 2.5, of from 0.75 to 2.25, of from 1.0 to 2.0, or of from 1.25 to 1.75, inches. Of course, still other lengths of the first fiber are contemplated.

In one embodiment, the second fiber has a length of from 2.0 to 4.0 inches. In another embodiment, the second fiber has a length of from 2.5 to 3.5 inches. In other embodiments, the second fiber has a length of from 1.0 to 5.0, of from 2.0 to 5.0, of from 3.0 to 5.0, or of from 4.0 to 5.0, inches. In still other embodiments, the second fiber has a length of from 1.0 to 4.0, 1.0 to 3.0, or of from 1.0 to 2.0 inches. In still other embodiments, the second fiber has a length of from 2.25 to 3.75, of from 2.5 to 3.5, or of from 2.75 to 3.25 inches. Of course still other lengths of the second fiber are contemplated. It will be readily appreciated that the second fiber may have the same length as the first fiber, or within any of the ranges described herein for the first fiber. Moreover, the first fiber may have a length within any of the ranges described herein for the second fiber.

In one embodiment, the first fiber may have a denier of from 0.5 to 2.5. In another embodiment, the first fiber may have a denier 1.0 to 2.0. In other embodiments, the first fiber may have a denier of from 0.75 to 2.5, of from 1 to 2.5, of from 1.25 to 2.5, of from 1.5 to 2.5, of from 1.75 to 2.5, of from 2.0 to 2.5, or of from 2.25 to 2.5. In still other embodiments, the first fiber may have a denier of from 0.5 to 2.25, of from 0.5 to 2.0, of from 0.5 to 1.75, of from 0.5 to 1.5, of from 0.5 to 1.25, of from 0.5 to 1.0, or of from 0.5 to 0.75. In still other embodiments, the first fiber has a denier of from 0.8 to 1.5, or of from 1.0 to 1.3. Of course, still other deniers of the first fiber are contemplated.

In one embodiment, the second fiber may have a denier of from 4.5 to 5.0. In another embodiment, the second fiber may have a denier of from 4.0 to 6.0. In other embodiments, the second fiber may have a denier of from 4.25 to 6.0, of from 4.5 to 6.0, of from 4.75 to 6.0, of from 5.0 to 6.0, of from 5.25 to 6.0, of from 5.5 to 6.0, or of from 5.75 to 6.0. In still other embodiments, the second fiber may have a denier of from 4.0 to 5.75, of from 4.0 to 5.5, of from 4.0 to 5.25, of from 4.0 to 5.0, of from 4.0 to 4.75, of from 4.0 to 4.5, or of from 4.0 to 4.25. In still other embodiments, the second fiber may be have a denier of from 4.0 to 5.0, or of from 4.25 to 5.0. Of course, still other deniers of the second fiber are contemplated. It will be readily appreciated that the second fiber may have the same denier as the first fiber, or within any of the ranges described herein for the first fiber. Moreover, the first fiber may have a denier within any of the ranges described herein for the second fiber.

In some embodiments, when the cloth comprises the first fiber and the second fiber, the first fiber may be included in an amount of from 40 to 99, of from 50 to 90, of from 60 to 80, or of from 65 to 75, wt. % based on the total weight of the cloth, and the second fiber may be included in an amount of from 1 to 60, of from 10 to 50, of from 20 to 40, or of from 25 to 35, wt. % based on the total weight of the cloth. In other embodiments, the first fiber and the second fiber may be included in the same amount. In still other embodiments, the first fiber and the second fiber are not included in the same amount.

In one specific embodiment, the cloth 24 comprises the first fiber and the second fiber, with the first fiber comprising polyester fiber and the second fiber comprising polyester fiber. The first fiber has a length of from 1.0 to 3.0 inches and a denier of from 1.2 to 2.0. The second fiber has a length of from 3.0 to 4.0 inches and a denier of from 4.0 to 5.0. The first fiber is included in an amount of from 60 to 80 wt. % based on the total weight of the cloth 24. The second fiber is included in an amount of from 20 to 40 wt. % based on the total weight of the cloth 24. The cloth 24 has a thickness of from 0.055 to 0.125. The cloth 24 has a weight of from 3.8 to 5.8 ounces per square yard. The cloth 24 has a tensile strength of at least 27 pounds per square inch in a given direction, with the given direction correlating with a machining direction of the cloth 24.

When the applicator 24 comprises the non-woven cloth 24, the non-woven cloth 24 may be produced using any suitable method of producing a non-woven cloth as described herein. When the non-woven cloth 24 comprises a first fiber and a second fiber, the method of making the non-woven cloth may comprise blending the first and second fiber together to form blended fibers. The method may further comprise carding the blended fibers to form carded fibers, followed by crosslapping and then needle punching of the carded fibers to form a sheet of non-woven cloth. Thus, the first fiber and the second fiber are mechanically intertwined by needle punching. The sheet of non-woven cloth may then be cut into individual non-woven cloths. The non-woven cloth may, by way of non-limiting example, have a length of from 5 to 15 inches and a width of from 5 to 15 inches. In some embodiments, the length of the non-woven cloth may be equal to the width of the non-woven cloth. In other embodiments, the length and the width may be different. Of course, still other methods of producing the non-woven cloth 24 are contemplated.

In some embodiments, the method of producing a non-woven cloth may further comprise folding the sheet of non-woven cloth. By way of non-limiting example, the non-woven cloth may be folded in a "z-fold" (also known as an "s-fold"), a "c-fold," or any other fold style suitable for the non-woven cloth. With reference to FIGS. 3 and 4, in the illustrated embodiment, the non-woven cloth 24 is folded in a "z-fold." Of course, it is contemplated that in some embodiments the non-woven cloth may not be folded.

As described above, the applicator may comprise foam. The foam may comprise an open-celled foam or a closed-cell foam. The foam may comprise synthetic polymers. In some embodiments, when the foam comprises synthetic polymers, the synthetic polymers may be selected from the group comprising polyurethanes, polyesters, polyalkylenes, polyols, or combinations thereof. Of course, still other synthetic polymers are contemplated. Additionally, the foam may comprise natural polymers in other embodiments.

The antiseptic composition comprises one or more antibacterial agents and one or more solvents. As such, when applied to the skin or mucous membranes of a patient, the antiseptic composition is capable of killing or inhibiting the growth of bacteria on the skin or mucous membranes of the patient. In this manner, the antiseptic composition is suitable for disinfecting the skin or mucous membranes of a patient, particularly prior to a surgical operation.

The antibacterial agent may comprise chlorhexidine. The chlorhexidine may be free base chlorhexidine or a pharmaceutically acceptable salt of chlorhexidine. When the chlorhexidine is a pharmaceutically acceptable salt of chlorhexidine, the chlorhexidine may be, chlorhexidine dihydrochloride, chlorhexidine diacetate, chlorhexidine digluconate (also known as chlorhexidine gluconate, or CHG), chlorhexidine dilactate, chlorhexidine digalactate, or combinations thereof. In certain embodiments, the antibacterial agent is CHG. The pharmaceutically acceptable salt of chlorhexidine may be selected based on the solvent of the antiseptic composition due to the solubility properties of the pharmaceutically acceptable salt of chlorhexidine. For instance, CHG is soluble in water whereas chlorhexidine diacetate is substantially insoluble in water and is therefore more suitable for non-aqueous solvents.

It will be appreciated that the antibacterial agent may comprise compounds other than chlorhexidine such as, by way of non-limiting example, aminoglycoside compounds, polyhexanide, triclosan, quaternary ammonium compounds such as cetrimide, proflavine hemisulphate, chlorocresol, chlorophene, chloroxylenol, iodine, iodophors, etc., and combinations thereof. Of course, still other antibacterial agents are contemplated. Thus, while the term 'chlorhexidine' is used as an adjective throughout this disclosure to describe the product, article and other components thereof, it should be appreciated that products/articles may be free from chlorhexidine components if other antibacterial agents are utilized.

The antibacterial agent may be included in the antiseptic composition in an amount of from 0.1 to 10 wt. % based on the total weight of the antiseptic composition. In another embodiment, the antibacterial agent may be included in an amount of from 1.5 to 5.0 wt. % based on the total weight of the antiseptic composition. In other embodiments, the antibacterial agent may be included in an amount from 0.5 to 10, of from 1.0 to 10, of from 1.5 to 10, of from 2.0, to 10, of from 2.5 to 10, of from 3.0 to 10, of from 3.5 to 10, of from 4.0 to 10, of from 4.5 to 10, of from 5.0 to 10, of from 5.5 to 10, of from 6.0 to 10, of from 6.5 to 10, of from 7.0 to 10, of from 7.5 to 10, of from 8.0 to 10, of from 8.5 to 10, of from 9.0 to 10, or of from 9.5 to 10 wt. % based on the total weight of the antiseptic composition. In still other embodiments, the antibacterial agent may be included in the antiseptic composition in an amount of from 0.1 to 9.5, of from 0.1 to 9.0, of from 0.1 to 8.5, of from 0.1 to 8.0, of from 0.1 to 7.5, of from 0.1 to 7.0, of from 0.1 to 6.5, of from 0.1 to 6.0, of from 0.1 to 5.5, of from 0.1 to 5.0, of from 0.1 to 4.5, of from 0.1 to 4.0, of from 0.1 to 3.5, of from 0.1 to 3.0, of from 0.1 to 2.5, of from 0.1 to 2.0, of from 0.1 to 1.5, of from 0.1 to 1.0, or of from 0.1 to 0.5, wt. % based on the total weight of the antiseptic composition. In still other embodiments, the antibacterial agent may be included in the antiseptic composition in an amount of from 0.5 to 8.0, of from 1.0 to 6.0, of from 1.5 to 5.0, of from 1.8 to 4.5, of from 1.8 to 3.5, or of from 1.8 to 2.5, wt. % based on the total weight of the antiseptic composition. The amount of antibacterial agent may vary outside of the ranges above, but is typically both whole and fractional values within these ranges. Further, it is to be appreciated that more than one antibacterial agent may be included in the antiseptic composition, in which case the total amount of all the antibacterial agents included is within the above ranges.

The solvent may comprise an aqueous solvent, a non-aqueous solvent, or combinations thereof. In certain embodiments, when the solvent comprises an aqueous solvent, the solvent may be water. The water may be distilled water, sterile water, purified water prepared in accordance with United States Pharmacopeia (USP) standards, or any other type of water that is suitable for use in antiseptic compositions.

In other embodiments, when the solvent is a non-aqueous solvent, the solvent may be an alcohol. Examples of alcohols suitable for the antiseptic composition include, by way of non-limiting example, ethanol or isopropyl alcohol. Of course, still other solvents are contemplated.

The solvent may be included in the antiseptic composition in an amount of at least 1 wt. % based on the total weight of the antiseptic composition. In another embodiment, the solvent may be included in the antiseptic composition an amount of at least 50 wt. % based on the total weight of the antiseptic composition. In other embodiments, the solvent may be included in the antiseptic composition in amount of at least 5, at least 10, at least 20, at least 30, at least 40, at least 50, at least 60, at least 70, at least 80, at least 90, at least 95, or at least 99, wt. % based on the total weight of the antiseptic composition. In still other embodiments, the solvent may be included in the antiseptic composition in an amount less than 99, less than 95, less than 90, less than 80, less than 70, less than 60, less than 50, less than 40, less than 30, less than 20, less than 10, or less than 5, wt. % based on the total weight of the antiseptic composition. In still other embodiments, the solvent is included in an amount of from 40 to 99, of from 50 to 95, of from 60 to 90, of from 65 to 85, or of from 75 to 85 wt. % based on the total weight of the antiseptic composition. The amount of solvent may vary outside of the ranges above, but is typically both whole and fractional values within these ranges. Further, it is to be appreciated that more than one solvent may be included in the antiseptic composition, in which case the total amount of all the solvents included is within the above ranges.

In certain embodiments, when the solvent is water, water may be included in the antiseptic composition in an amount of at least 50 wt. % based on the total weight of the antiseptic composition. In another embodiment, water may be included in the antiseptic composition in an amount of at least 60 wt. % based on the total weight of the antiseptic composition. In other embodiments, water may be included in the antiseptic composition in an amount of at least 65, at least 70, at least 75, or at least 80, wt. % based on the total weight of the antiseptic composition. In still other embodiments, water may be included in the antiseptic composition in an amount of from 50 to 99, of from 60 to 95, of from 70 to 90, of from 75 to 90, or of from 80 to 90, wt. % based on the total weight of the antiseptic composition. The amount of water may vary outside of the ranges above, but is typically both whole and fractional values within these ranges. Further, it is to be appreciated that more than one type of water may be included in the antiseptic composition, in which case the total amount of all the types of water included is within the above ranges.

In some embodiments, at least 95% of the antibacterial agent is dissolved in the solvent of the antiseptic composition. In other embodiments, at least 50, 60, 70, 80, 90, 99, wt. % of the antibacterial agent is dissolved in the solvent of the antiseptic composition. It is further contemplated that all of the antibacterial agent may be dissolved in the solvent of the antiseptic composition.

The antiseptic composition may further comprise a humectant. The humectant may be compatible for use in the antiseptic composition, particularly in view of the antibacterial agent included in the antiseptic composition. The humectant may be, by way of non-limiting example, glycerol prepared according to USP standards (USP glycerol), propylene glycol, polyethylene glycol, N-methyl pyrrolidone, N-ethyl pyrrolidone, diacetone alcohol, γ-butyryl lactone, ethyl lactate, low molecular weight polyethylene glycol, and combinations thereof. In certain embodiments, the humectant comprises USP glycerol and propylene glycol. Of course, other types of humectants are contemplated such as, by way of non-limiting example, monosaccharides, disaccharides, castor oil and derivatives and salts thereof, vegetable oil extracts such as triglycerides, and combinations thereof. Of course, still other humectants are contemplated.

When present, the humectant may be included in the antiseptic composition in an amount less than 20 wt. % based on the total weight of the antiseptic composition. In another embodiment, the antiseptic composition is included in an amount of from 3.0 to 10 wt. % based on the total weight of the antiseptic composition. In other embodiments, the humectant is included in the antiseptic composition in an amount less than 17.5, less than 15, less than 12.5, less than 10, less than 7.5, less than 5.0, or less than 2.5, wt. % based on the total weight of the antiseptic composition. In still other embodiments, the humectant is included in an amount of at least 2.5, at least 5.0, at least 7.5, at least 10, at least 12.5, at least 15, at least 17.5, or at least 20, wt. % based on the total weight of the antiseptic composition. In still other embodiments, the humectant is included in the antiseptic composition in an amount of from 3.5 to 9.0, of from 4.0 to 8.0, of from 4.5 to 7.0, or of from 5.0 to 6.0, wt. % based on the total weight of the antiseptic composition. The amount of humectant may vary outside of the ranges above, but is typically both whole and fractional values within these ranges. Further, it is to be appreciated that more than one humectant may be included in the antiseptic composition, in which case the total amount of all the humectants included is within the above ranges. For example, the humectant may comprise USP glycerol in an amount of from 2.0 to 3.0 wt. % based on the total weight of the antiseptic composition and propylene glycol in an amount of from 2.5 to 3.5 wt. % based on the total weight of the antiseptic composition.

The antiseptic composition may further comprise an emollient. The emollient may be of any type that is suitable for topical application to a patient. The emollient may be, by way of non-limiting example, petroleum-based oils, petrolatum, vegetable oils, mineral oils, lanolin and derivatives thereof, glycerol esters and derivatives thereof, fatty esters, propylene glycol esters and derivatives thereof, alkoxylated carboxylic acids, aloe vera, fatty alcohols, dimethicone, alkyl methicones, alkyl dimethicones, phenyl silcones, alkyl trimethylsilanes, and combinations thereof. In certain embodiments, the emollient comprises dimethicone and aloe vera. Of course, still other emollients are contemplated.

When present, the emollient or other components of the antiseptic composition may comprise insoluble particles. In the context of this disclosure "insoluble particles" are particles that are not soluble in the solvent of the antiseptic composition. In certain embodiments, the insoluble particles have an average diameter of greater than 0.2 microns such that the antiseptic composition may not be sterilized by filtration because the insoluble particles are too large.

When present, the emollient may be included in the antiseptic composition in an amount less than 10 wt. % based on the total weight of the antiseptic composition. In another embodiment, the emollient may be included in the antiseptic composition an amount less than 5 wt. % based on the total weight of the antiseptic composition. In other embodiments, the emollient is included in the antiseptic composition in an amount less than 2.5, less than 2.0, less than 1.5, less than 1.0, less than 0.5, less than 0.25, or less than 0.2, wt. % based on the total weight of the antiseptic composition. Alternatively, the antiseptic composition comprises an amount of emollient of from 0.01 to 1, 0.1 to 0.25, or 0.1 to 0.2, wt. % based on the total weight of the antiseptic composition. The amount of emollient may vary outside of the ranges above, but is typically both whole and fractional values within these ranges. Further, it is to be appreciated that more than one emollient may be included in the antiseptic composition, in which case the total amount of all the emollients included is within the above ranges.

The antiseptic composition may further comprise a surfactant. The surfactant may be any surfactant that is compatible with the antibacterial agent of the antiseptic composition. Depending on the antibacterial agent included in the antiseptic composition, the surfactant may be a cationic surfactant, an anionic surfactant, non-ionic surfactant, or combinations thereof. When the surfactant is a non-ionic surfactant, the non-ionic surfactant may be, by way of non-limiting example, polysorbate 20, polysorbate 40, polysorbate 60, polysorbate 80, polysorbate 120, a polyoxyethylene alkyl ether, polyoxyethylene cetyl ether, polyoxyethylene palmityl ether, polyoxyethylene oxide hexadecyl ether, polyethylene glycol cetyl ether, a sucrose ester, a partial ester of sorbitol, a monoglyceride, a diglyceride, di- and tri-esters of sucrose with fatty acid, nonylphenol ethoxylate (Igepal CO 630), nonoxynol-9 and combinations thereof. In certain embodiments, the surfactant comprises polysorbate 20 and Igepal CO 630. Of course, still other surfactants are contemplated.

When present, the surfactant may be included in the antiseptic composition in an amount less than 5.0 wt. % based on the total weight of the antiseptic composition. In another embodiment, the surfactant may be included in the antiseptic composition in an amount less than 2.5 wt. % based on the total weight of the antiseptic composition. In other embodiments, the surfactant may be included in the antiseptic composition in an amount less than 2.0, less than 1.5, less than 1.0, less than 0.75, less than 0.50, less than 0.25, less than 0.2, less than 0.15, or less than 0.1, wt. % based on the total weight of the antiseptic composition. Alternatively, the surfactant may be included in the antiseptic composition in an amount of from 0.01 to 2, 0.05 to 1.5, or 0.01 to 0.75, wt. % based on the antiseptic composition. The amount of surfactant may vary outside of the ranges above, but is typically both whole and fractional values within these ranges. Further, it is to be appreciated that more than one surfactant may be included in the antiseptic composition, in which case the total amount of all the surfactants included is within the above ranges.

The antiseptic composition may further comprise a pH adjuster. The pH adjuster may be any pH adjuster compatible for use in the antiseptic composition. The pH adjuster may be, by way of non-limiting example, adipic acid and derivatives thereof, glycine and derivatives thereof, citric acid and derivatives thereof, calcium hydroxide, magnesium aluminometasilicate, glucono delta lactone, or combinations thereof. In certain embodiments, the pH adjuster is glucono delta lactone. Of course, still other pH adjusters are contemplated.

When present, the pH adjuster may be included in the antiseptic composition in an amount less than 5 wt. % based on the total weight of the antiseptic composition. In another embodiment, the pH adjuster may be included in the antiseptic composition in an amount less than 2.5 wt. % based on the total weight of the antiseptic composition. In other embodiments, the pH adjuster may be included in the antiseptic composition in an amount less than 2.0, less than 1.5, less than 1.0, less than 0.75, less than 0.50, less than 0.25, less than 0.2, less than 0.15, or less than 0.1, wt. % based on the total weight of the antiseptic composition. Alternatively, the pH adjuster may be included in the antiseptic composition in an amount of from 0.01 to 2, 0.05 to 1.5, or 0.05 to 0.5, wt. % based on the antiseptic composition. The amount of pH adjuster may vary outside of the ranges above, but is typically both whole and fractional values within these ranges. Further, it is to be appreciated that more than one pH adjuster may be included in the antiseptic composition, in which case the total amount of all the pH adjusters included is within the above ranges.

The antiseptic composition may have any pH suitable for the antiseptic composition to be used to disinfect the skin or mucous membranes of a patient, particularly in view of the antibacterial agent included in the antiseptic composition. In one embodiment, the antiseptic composition may have a pH of from 4 to 6. In another other embodiment, the antiseptic composition may have a pH of from 4.2 to 5.2. In still other embodiment, the antiseptic composition may have a pH of from 4 to 8, of from 4 to 7, of from 4 to 6, or of from 4 to 5. The pH of the antiseptic composition may vary outside of the ranges above in specific embodiments, but is typically both whole and fractional values within these ranges.

The antiseptic composition may further comprise an odorant. The odorant may be any odorant suitable for use in the antiseptic composition. The odorant may be, by way of non-limiting example, perfumes, fragrances, ethereal oils, essences, scents, and combinations thereof. Of course, still other odorants are contemplated.

When present, the odorant may be included in the antiseptic composition in an amount less than 5 wt. % based on the total weight of the antiseptic composition. In another embodiment, the odorant may be included in the antiseptic composition in an amount less than 2.5 wt. % based on the total weight of the antiseptic composition. In other embodiments, the odorant may be included in the antiseptic composition in an amount less than 2.0, less than 1.5, less than 1.0, less than 0.75, less than 0.50, less than 0.25, less than 0.2, less than 0.15, or less than 0.1, wt. % based on the total weight of the antiseptic composition. Alternatively, the odorant may be included in the antiseptic composition in an amount of from 0.001 to 2, 0.005 to 1.5, or 0.005 to 0.5, wt. % based on the antiseptic composition. The amount of odorant may vary outside of the ranges above, but is typically both whole and fractional values within these ranges. Further, it is to be appreciated that more than one odorant may be included in the antiseptic composition, in which case the total amount of all the odorants included is within the above ranges.

The antiseptic composition may further comprise a colorant. The colorant may be any colorant suitable for use in the antiseptic composition. The colorant may be a synthetically derived colorant or a naturally derived colorant. The colorant may be, by way of non-limiting example, Brilliant Blue FCF, Fast Green FCF, indigo carmine, carmoisine lake, erythrosine, carmine lake, tartrazine, annatto, colorants produced by converting a naturally derived colorant to an aluminum or calcium salt, and combinations thereof. Of course, still other colorants are contemplated.

When present, the colorant may be included in the antiseptic composition in an amount less than 5 wt. % based on the total weight of the antiseptic composition. In another embodiment, the colorant may be included in the antiseptic composition in an amount less than 2.5 wt. % based on the total weight of the antiseptic composition. In other embodiments, the colorant may be included in the antiseptic composition in an amount less than 2.0, less than 1.5, less than 1.0, less than 0.75, less than 0.50, less than 0.25, less than 0.2, less than 0.15, or less than 0.1, wt. % based on the total weight of the antiseptic composition. Alternatively, the colorant may be included in the antiseptic composition in an amount of from 0.001 to 2, 0.005 to 1.5, or 0.005 to 0.5, wt. % based on the antiseptic composition. The amount of colorant may vary outside of the ranges above, but is typically both whole and fractional values within these ranges. Further, it is to be appreciated that more than one colorant may be included in the antiseptic composition, in which case the total amount of all the colorants included is within the above ranges.

The antiseptic composition may further comprise a stabilizer, a skin protectant, a preservative, or combinations thereof. When present, the stabilizer, the skin protectant, and/or the preservative may each be included in the antiseptic composition in amounts of less than 5 wt. % based on the total weight of the antiseptic composition. In another embodiment, the stabilizer, the skin protectant, and/or the preservative may each be included in the antiseptic composition in an amount less than 2.5 wt. % based on the total weight of the antiseptic composition. In other embodiments, the stabilizer, the skin protectant, and/or the preservative may be each included in the antiseptic composition in an amount less than 2.0, less than 1.5, less than 1.0, less than 0.75, less than 0.50, less than 0.25, less than 0.2, less than 0.15, or less than 0.1, wt. % based on the total weight of the antiseptic composition. Alternatively, the stabilizer, the skin protectant, and/or the preservative may each be included in the antiseptic composition in an amount of from 0.001 to 2, 0.01 to 1.5, or 0.01 to 0.5, wt. % based on the antiseptic composition. The amount of the stabilizer, the skin protectant, and/or the preservative may vary outside of the ranges above, but is typically both whole and fractional values within these ranges. Further, it is to be appreciated that more than one of the stabilizer, the skin protectant, and/or the preservative may be included in the antiseptic composition, in which case the total amount of all the stabilizers, the skin protectants, and/or the preservatives included is within the above ranges.

In one particular embodiment, the antiseptic composition includes less than 10, 5, 3, 1, 0.5, or 0.1, wt. % of an anionic compound. For configurations where the antibacterial agent comprises CHG, anionic compounds may compromise the efficacy of the antiseptic composition. As such, the selection of the components included in the antiseptic composition may account for this characteristic. For example, in embodiments where the antiseptic composition includes at least one of the humectant, the emollient, the surfactant, the pH adjuster, the odorant, the colorant, the stabilizer, the preservative, and/or the skin protectant, each of these components included may be non-ionic or cationic. In still further embodiments, the antiseptic composition may be free of an anionic compound other than the anionic compound(s) included as the antibacterial agent. In other words, no anionic compound may be included in the antiseptic composition, other than those anionic compounds of the antibacterial agent.

In some embodiments, the antiseptic composition is free of an alcohol having a boiling point less than 90° C. at 1.0 atm. By way of non-limiting example, an alcohol having a boiling point less than 90° C. at 1.0 atm may be ethanol or isopropyl alcohol. Alternatively, the antiseptic composition may include less than 5.0 wt. % alcohol having a boiling point less than 90° C. at 1.0 atm based on the total weight of the antiseptic composition. Alternatively still, the antiseptic composition includes less than 4.0 wt. %, less than 3.0 wt. %, less than 2.0 wt. %, or less than 1.0 wt. %, of alcohol having a boiling point less than 90° C. at 1.0 atm, each based on the total weight of the antiseptic composition. In these embodiments, the antiseptic composition is particularly suitable for disinfection of the skin or mucous membranes of a patient because the antiseptic composition does not dry the skin or mucous membranes of the patient. Moreover, the antiseptic composition may be applied to the skin or mucous membranes of a patient multiple times within a 24 hour period without concern for irritating the skin or mucous membranes of the patient due to dryness. However, despite the fact that an alcohol having a boiling point less than 90° C. at 1.0 atm is generally not necessary, in certain embodiments, the antiseptic composition may include an alcohol having a boiling point less than 90° C. at 1.0 atm in an amount of from 5 to 15 wt. % based on the total weight of the antiseptic composition.

The antiseptic composition may include less than 10, less than 7.5, less than 5.0, less than 2.5, less than 1.0, or less than 0.5 wt. % of an alcohol based on the total weight of the antiseptic composition wt. % of an alcohol based on the total weight of the antiseptic composition. Alternatively, the antiseptic composition includes no amount of an alcohol. In these embodiments, the antiseptic composition is particularly suitable for disinfection of the skin or mucous membranes of a patient because the antiseptic composition does not dry the skin or mucous membranes of the patient. Of course, it will be appreciated that in some embodiments, alcohol may be included in the antiseptic composition in amounts greater than 10 wt. % based on the total weight of the antiseptic composition.

In some embodiments, the antiseptic composition is non-flammable. The antiseptic composition may be non-flammable such that the flash point of the antiseptic composition is at least 38° C., at least 60° C., or at least 93° C. In this manner, the antiseptic composition of the chlorhexidine article reduces the potential risk of fire that may be associated with other antiseptic compositions such as those that contain, for example, ethanol or isopropyl alcohol.

In one particular embodiment, the antiseptic composition comprises water in an amount of at least 50 wt. % based on the total weight of the antiseptic composition and chlorhexidine gluconate (CHG) in an amount of from 1.5 to 5.0 wt. % based on the total weight of the antiseptic composition. The CHG is dissolved in the water. In another embodiment, the antiseptic composition consists essentially of water in an amount of at least 50 wt. % based on the total weight of the antiseptic composition, chlorhexidine gluconate (CHG) in an amount of from 1.5 to 5.0 wt. % based on the total weight of the antiseptic composition, a humectant in an amount of from 3.0 to 10 wt. % based on the total weight of the antiseptic composition, an emollient in an amount less than 1.0 wt. % based on the total weight of the antiseptic composition, and optionally additives selected from the group consisting of a solvent, an antibacterial agent, a humectant, an emollient, a surfactant, a pH adjuster, an odorant, a colorant, or combinations thereof.

In various embodiments, the antiseptic composition is, comprises, or consists essentially of an antibacterial agent and a solvent. For example, in embodiments that "consist essentially of" the aforementioned components, the antiseptic composition may be free of the humectant, the emollient, the surfactant, the pH adjuster, the odorant, the colorant, the stabilizer, the skin protectant, the preservative, and/or combinations thereof. Alternatively, any one or more of these components may be included in an amount less than 25, 20, 15, 10, 5, 4, 3, 2, 1, 0.1, 0.05, 0.01, etc., wt. % or any range thereof, based on a total weight of the antiseptic composition. In various non-limiting embodiments, all values and ranges of values between the aforementioned values are hereby expressly contemplated.

It should be appreciated that the ranges provided above for each of the components of the antiseptic compositions may refer to the amounts of those components in the sterilized antiseptic compositions or the unsterilized antiseptic compositions. Because certain sterilization processes may cause certain components to degrade, the amount of each component in the antiseptic composition may vary from the non-sterile condition to the sterilized condition. As but one example, the description provided above should be understood to encompass the possibility that the sterilized antiseptic composition may comprise an amount of from 0.1 to 5 wt. % of the antibacterial agent, or alternatively, that the unsterilized antiseptic composition may comprise an amount of from 0.1 to 5 wt. % of the antibacterial agent.

Referring again to FIG. 4, in certain embodiments, the antiseptic composition is impregnated in the applicator 24. In some embodiments, when the antiseptic composition is impregnated in the applicator 24, the antiseptic composition may be dispersed evenly in the applicator 24 such that the concentration of the antiseptic composition is substantially the same (+/−1, 3, 5, or 10 wt. %) at all regions of the applicator 24. In other embodiments, the antiseptic composition may be impregnated in the applicator 24 such that a region of the applicator 24 may have a greater concentration of the antiseptic composition than another region. By way of non-limiting example, the antiseptic composition may be impregnated in the applicator 24 such that the concentration of the antiseptic composition is greater at a surface of the applicator 24 than beneath the surface of the applicator, or vice-versa.

As will be described in further detail below, in some embodiments, when the antiseptic composition is impregnated in the applicator 24, the antiseptic composition may be impregnated in the applicator 24 an amount of from 0.1 to 100 g per applicator. In another embodiment, the antiseptic composition may be impregnated in the applicator 24 in an amount of from 15 to 40 g per applicator. In other embodiments, the antiseptic composition may be impregnated in the applicator 24 in an amount of from 0.1 to 90, of from 0.1 to 80, of from 0.1 to 70, of from 0.1 to 60, of from 0.1 to 50, of from 0.1 to 40, of from 0.1 to 30, of from 0.1 to 20, of from 0.1 to 10, of from 0.1 to 5, or of from 0.1 to 2.5, g. In still other embodiments, the antiseptic composition may be impregnated in the applicator 24 in an amount of from 2.5 to 100, of from 5 to 100, of from 10 to 100, of from 20 to 100, of from 30 to 100, of from 40 to 100, of from 50 to 100, of from 60 to 100, of from 70 to 100, of from 80 to 100, of from 90 to 100, g. In still other embodiments, the antiseptic composition may be impregnated in the applicator 24 in an amount of from 5 to 50 g, of from 10 to 40, of from 15 to 30, or of from 22.5 to 27.5, g.

In some embodiments, the antiseptic composition may be impregnated in the applicator 24 in an amount of from 0.1 to 100 mL per applicator. In another embodiment, the antiseptic composition may be impregnated in the applicator 24 in an amount of from 15 to 40 mL per applicator. In other embodiments, the antiseptic composition may be impregnated in the applicator 24 in an amount of from 0.1 to 90, of from 0.1 to 80, of from 0.1 to 70, of from 0.1 to 60, of from 0.1 to 50, of from 0.1 to 40, of from 0.1 to 30, of from 0.1 to 20, of from 0.1 to 10, of from 0.1 to 5, or of from 0.1 to 2.5, mL. In still other embodiments, the antiseptic composition may be impregnated in the applicator 24 in an amount of from 2.5 to 100, of from 5 to 100, of from 10 to 100, of from 20 to 100, of from 30 to 100, of from 40 to 100, of from 50 to 100, of from 60 to 100, of from 70 to 100, of from 80 to 100, of from 90 to 100, mL. In still other embodiments, the antiseptic composition may be impregnated in the applicator 24 in an amount of from 5 to 50 g, of from 10 to 40, of from 15 to 30, or of from 22.5 to 27.5, mL.

The antiseptic composition may be impregnated in the applicator 24 in an amount such that the concentration of the antibacterial agent is therapeutically effective in each applicator. In one embodiment, the antiseptic composition is impregnated in the applicator 24 such that antibacterial agent is included in an amount of from 50 to 1000 mg per applicator 24. In other embodiments, the antiseptic composition is impregnated in the applicator 24 such that antibacterial agent is included in an amount of from 100 to 900, 200 to 800, 300 to 700, 400 to 600, or 450 to 550, mg per applicator 24. In certain embodiments, when CHG is the antibacterial agent, the antiseptic composition may be impregnated in the applicator 24 such that CHG is included in an amount of from 400 to 600 mg per applicator 24.

In instances where the applicator is not impregnated, but rather includes a receptacle for retaining the antiseptic composition before activation by the caregiver, each receptacle may comprise the antiseptic composition in an amount of from 0.1 to 100, 15 to 40, 0.1 to 90, 0.1 to 80, 0.1 to 70, 0.1 to 60, 0.1 to 50, 0.1 to 40, 0.1 to 30, 0.1 to 20, 0.1 to 10, 0.1 to 5, 0.1 to 2.5 g per receptacle. The antiseptic composition may be included in the receptacle such that the antibacterial agent is included in an amount of from 100 to 900, 200 to 800, 300 to 700, 400 to 600, or 450 to 550, mg per receptacle.

In some embodiments, the chlorhexidine product may further comprise an insert. The insert may be disposed in the package to support the chlorhexidine article and insulate the chlorhexidine article. As an example, the insert may insulate the chlorhexidine article disposed in the package during heating of the chlorhexidine article prior to application of the chlorhexidine article to the skin or mucous membranes of a patient. Furthermore, the insert may be used to support the applicator when the applicator is impregnated with the antiseptic composition. In this manner, the insert may ensure the applicator does not become contaminated during impregnation of the antiseptic composition.

As will be described below, the chlorhexidine article 14 undergoes a sterilization process, such as a terminal sterilization process, to form a sterilized chlorhexidine article 14. The chlorhexidine article 14 may be subjected to any sterilization process suitable to sterilize the chlorhexidine article 14 such that the sterility of the chlorhexidine article 14 can be validated. For example, the chlorhexidine article 14 may be subjected to heat sterilization, radiation sterilization, ethylene oxide gas sterilization, or combinations thereof.

In the context of this disclosure, when the chlorhexidine article 14 is sterilized, the components of the chlorhexidine article 14 are in a sterile condition, and that sterile condition has been validated, the resultant article is referred to as a sterilized chlorhexidine article 14. Accordingly, when the chlorhexidine article 14 is in the sterile condition, the applicator 24, the antiseptic composition, and components thereof, are referred to as a 'sterilized' applicator 24 and a 'sterilized' antiseptic composition, etc.

The sterile condition of the chlorhexidine article 14, or components thereof, may be defined as sterile in accordance with one or more ISO standards. By way of non-limiting example, the sterilized chlorhexidine article 14 may be sterile in accordance with ISO 20857, ISO 17665, ISO 11135, and/or ISO 11137. In some embodiments, the sterilized chlorhexidine article 14 may be sterile in accordance with ISO 11137.

When the chlorhexidine article 14, or components thereof, is exposed to a sterilization process, the sterilized chlorhexidine article 14, or components thereof, has a Sterility Assurance Level (SAL) equal to or less than $10^{-3}$. In the context of this disclosure, "SAL" means the probability of a chlorhexidine article 14 being in a non-sterile condition after the chlorhexidine article 14 has been subjected to a sterilization process (and remains in the package 12 free from further external contamination).

In one aspect, the sterilization process may be understood as a step or sequence of steps that are sufficient to give the chlorhexidine article 14 a SAL equal to or less than $10^{-3}$. In certain embodiments, the sterilized chlorhexidine article 14 has a SAL equal to or less than $10^{-6}$. In other embodiments, the sterilized chlorhexidine article 14 has a SAL of from $10^{-3}$ to $10^{-12}$, of from $10^{-3}$ to $10^{-9}$, or of from $10^{-3}$ to $10^{-6}$. In still other embodiments, the sterilized chlorhexidine article 14 has a SAL of from $10^{-6}$ to $10^{-12}$, or of from $10^{-9}$ to $10^{-12}$. In still other embodiments, the sterilized chlorhexidine article 14 has a SAL of less than $10^{-9}$, or less than $10^{-12}$. In some embodiments, the chlorhexidine article 14 has a SAL of from $10^{-3}$ to $10^{-9}$. As described above, the components of the sterilized chlorhexidine article 14 may also have a SAL corresponding to the SAL of the sterilized chlorhexidine article 14. For example, the sterilized water, the sterilized applicator 24, and the other components of the sterilized article may have a SAL of from $10^{-3}$ to $10^{-12}$, of from $10^{-3}$ to $10^{-9}$, or of from $10^{-3}$ to $10^{-6}$.

In one embodiment, when the chlorhexidine product 10 is subjected to a sterilization process, such as a terminal sterilization process, it will be appreciated that the package 12 is also subjected to the sterilization process in addition to the chlorhexidine article 14 disposed therein. However, as the external surface of the package 12 is exposed to the environment during subsequent handling (post-sterilizing), the external surface of the package 12 may not remain sterile even though the sterilized chlorhexidine article 14 does remain in the sterile condition. Despite the fact that the external surface of the package 12 may not remain sterile, the interior volume 16 of the package 12 remains sterile at least until the package 12 is opened. In the context of this disclosure, the term package 12 is used to refer to both a sterilized package 12 and a non-sterilized package 12.

When the chlorhexidine article is sterilized, the sterilized antiseptic composition may further comprise degradation impurities. The degradation impurities may be a result of exposing the chlorhexidine article to the sterilization process. When the sterilization process is heat sterilization, or radiation sterilization, and the antibacterial agent comprises CHG, the degradation impurities may include, by way of non-limiting example, N-[[6-[[[(4-chlorophenyl)carbamimidoyl]carbamimidoyl]-amino]hexyl]carbamimidoyl]urea, N-(4-chlorophenyl)guanidine, N-(4-chlorophenyl)urea, 1-(6-aminohexyl)-5-(4-chlorophenyl)biguanide, N-(4-chlorophenyl)-N'-[[6-[[[(4-chlorophenyl)carbamimidoyl]carbamimidoyl]amino]hexyl]carbamimidoyl]urea, 1-(4-chlorophenyl)-5-[6-[[(phenylcarbamimidoyl)carbamimidoyl]amino]hexyl]biguanide, 1-[6-(carbamimidoylamino)hexyl]-5-(4-chlorophenyl)-biguanide, p-chloroaniline, and combinations thereof. Of course still other degradation impurities of CHG are contemplated. Furthermore, degradation impurities for antibacterial agents other than CHG are also contemplated.

In one embodiment, the sterilized antiseptic composition is free from degradation impurities with a concentration having a toxicity unacceptable for topical skin applications according to ICH Q3. In one aspect, the sterilized antiseptic composition comprises less than 1, less than 0.1, less than 0.01, or less than 0.001 of a toxic degradation impurity.

When present, the degradation impurities may be included in the sterilized antiseptic composition in an amount less than 2.0 wt. % based on the total weight of the sterilized antiseptic composition. In another embodiment, the degradation impurities may be included in the sterilized antiseptic composition in an amount less than 5.0 wt. % based on the total weight of the sterilized antiseptic composition. In other embodiments, the degradation impurities may be included in the sterilized antiseptic composition in an amount less than 1.75, less than 1.5, less than 1.25, less than, 1.0, less than, 0.75, less than 0.5, less than 0.25, less than 0.2, less than 0.1, less than 0.05, less than 0.01, or less than 0.001 wt. % based on the total weight of the sterilized antiseptic composition. In still other embodiments, the degradation impurities may be included in the sterilized antiseptic composition in an amount of from 0.001 to 0.01, of from 0.001 to 0.1, of from 0.001 to 0.2, of from 0.001 to 0.25, of from 0.001 to 0.5, of from 0.001 to 0.75, of from 0.001 to 1.0, of from 0.001 to 1.25, of from 0.001 to 1.5, of from 0.001 to 1.75, or of from 0.001 to 2.0, wt. % based on the total weight of the sterilized antiseptic composition. The amount of degradation impurities may vary outside of the ranges above, but is typically both whole and fractional values within these ranges. Further, it is to be appreciated that more than one degradation impurity may be included in the antiseptic composition, in which case the total amount of all the degradation impurities included is within the above ranges.

The present disclosure also provides a method of sterilizing a chlorhexidine article.

The method of sterilizing the chlorhexidine article 14 comprises providing the applicator and providing the antiseptic composition. In some embodiments, providing the antiseptic composition may further comprise providing the solvent, providing the antibacterial agent, and combining the solvent and the antibacterial agent to form the antiseptic composition. In other embodiments, providing the antiseptic composition may further comprise providing the solvent, providing the antibacterial agent, providing at least one of the humectant, the emollient, the surfactant, the pH adjuster, the odorant, the colorant, the stabilizer, the skin protectant, or the preservative, and combining the solvent, the antibacterial agent, and the at least one of the humectant, the emollient, the surfactant, the pH adjuster, the odorant, the colorant, the stabilizer, the skin protectant, or the preservative, to form the antiseptic composition. It is contemplated that when at least one of the humectant, the emollient, the surfactant, the pH adjuster, the odorant, the colorant, the stabilizer, the skin protectant, or the preservative is provided, the solvent and the at least one of the humectant, the emollient, the surfactant, the pH adjuster, the odorant, the colorant, the stabilizer, the skin protectant, or the preservative may be combined first followed by combining the antibacterial agent, or in any other suitable order of addition. In some embodiments, the antibacterial agent may be combined with a portion of the solvent to form an antibacterial agent concentrate. By way of non-limiting example, the antibacterial agent concentrate may be 20 wt. % CHG dissolved in water. When the antibacterial agent concentrate is formed, the antibacterial agent concentrate may be combined with the solvent, or the solvent and at least one of the humectant, the emollient, the surfactant, the pH adjuster, the odorant, the colorant, the stabilizer, the skin protectant, or the preservative, to form the antiseptic composition.

The method may further comprise impregnating the antiseptic composition in the applicator 24 to form the chlorhexidine article 14. The antiseptic composition may be impregnated in the applicator 24 in any amount described herein to form the chlorhexidine article 14. Impregnating may be performed by spraying the antiseptic composition on the applicator on one or multiple sides. The amount of antiseptic composition that is impregnated may be appropriately metered to ensure that the proper amount is provided in each applicator. As described above, the applicator 24 may be support by an insert during impregnation to ensure applicator does not become contaminated during impregnation. Alternatively, when the applicator comprises the receptacle for receiving the antiseptic composition, the method of sterilizing the chlorhexidine article may comprise filling the receptacle of the applicator with the antiseptic composition to form the chlorhexidine article.

Once the antiseptic composition has been impregnated in the applicator 24, the chlorhexidine article 14 can be encompassed in the package 12. In one possible embodiment, the package 12 is wrapped around the chlorhexidine article 14 and prepared for sealing. However, it should be appreciated that other ways of encompassing the chlorhexidine article 14 in the package 12 may also be used.

The method further comprises sealing the chlorhexidine article 14 inside the package 12 to form the chlorhexidine product 10. The chlorhexidine article 14 may be sealed inside the package 12 such that the chlorhexidine article 14 is hermetically sealed inside the package 12. The chlorhexidine article 14 may be sealed inside the package 12 in any suitable manner such as, by way of non-limiting example, heat sealing. Of course, other methods of sealing the chlorhexidine article 14 inside the package 12 are contemplated. In some embodiments, the method of sterilizing the chlorhexidine article 14 may further comprise disposing the chlorhexidine article 14 within the interior volume 16 of the package 12 prior to sealing the chlorhexidine article 14 inside the package 12. In other embodiments, the method of sterilizing the chlorhexidine article 14 may further comprise disposing the package 12 about the chlorhexidine article 14 prior to sealing the chlorhexidine article 14 inside the package 12. In another embodiment, sealing the chlorhexidine article 14 inside the package 12 may comprise shrink wrapping the chlorhexidine article 14.

The method may further comprise cooling the chlorhexidine product 10. Because the chlorhexidine article 14 is disposed within the interior volume 16 of the package 12 at this point, the step of cooling may be further understood to include the step of cooling the chlorhexidine article 14 and components thereof, including but not limited to, the solvent, the antibacterial agent, etc. Cooling the chlorhexidine product 10 may further comprise cooling the chlorhexidine product 10 such that at least a portion of the solvent of the antiseptic composition undergoes a phase change from a liquid state to a solid state.

Cooling the chlorhexidine product 10 may comprise cooling the chlorhexidine product 10 to a temperature of from −100° C. to 20° C. In one embodiment, the chlorhexidine product 10 may be cooled to a temperature of from −30° C. to 3° C. In another embodiment, the chlorhexidine product 10 may be cooled to a temperature of from −80° C. to 5° C. In other embodiments, the chlorhexidine product 10 may be cooled to a temperature of from −90° C. to 20° C., of from −80° C. to 20° C., of from −70° C. to 20° C., of from −60° C. to 20° C., of from −50° C. to 20° C., of from −40° C. to 20° C., or of from −30° C. to 20° C. In certain embodiments, the chlorhexidine product 10 may be cooled to a temperature equal to or less than the freezing point of the solvent in the antiseptic composition. By way of non-limiting example, if the solvent comprises water, the chlorhexidine product 10 may be cooled to a temperature equal to or less than 0° C. Other suitable solvents and melting points are contemplated such as, by way of non-limiting example, ethanol (−114° C.), or isopropyl alcohol (−89° C.). When the solvent comprises more than one solvent, the chlorhexidine product 10 may be cooled to a temperature equal to or less than the melting point of the one of the solvents in the antiseptic composition. In still other embodiments, the chlorhexidine product 10 may be cooled to a temperature of from −40° C. to 10° C., of from −35° C. to 5° C., of from −30° C. to 0° C., or of from −25° C. to 10° C. In still other embodiments, the chlorhexidine product 10 may be cooled to a temperature of from −40° C. to 5° C., of from −40° C. to 0° C., of from −40° C. to −5° C., of from −40° C. to −10° C., of from −40° C. to −15° C., or of from −25° C. to −15° C. Of course, still other temperatures are contemplated.

In one aspect, cooling the chlorhexidine product 10 may comprise cooling the chlorhexidine product 10 such that at least 50 wt. % of the solvent of the antiseptic composition undergoes a phase change from a liquid state to a solid state. In another embodiment, cooling the chlorhexidine product 10 may comprise cooling the chlorhexidine product 10 such that at least 0.1 wt. % of the solvent of the antiseptic composition undergoes a phase change from a liquid state to a solid state. In other embodiments, cooling the chlorhexidine product 10 may comprise cooling the chlorhexidine product 10 such that at least 1, at least 5, at least 10, at least 15, at least 20, at least 30, at least 40, at least 50, at least 60, at least 70, at least 80, at least 90, at least 95, or at least 99, wt. % of the solvent undergoes a phase change from a liquid state to a solid state. In certain embodiments, cooling the chlorhexidine product 10 may comprise cooling the chlorhexidine product 10 such that all of the solvent undergoes a phase change from a liquid state to a solid state. Alternatively, cooling the chlorhexidine product 10 may comprise cooling the chlorhexidine product 10 such that none of the solvent undergoes a phase change from a liquid state to a solid state. In still other embodiments, cooling the chlorhexidine product 10 may comprise cooling the chlorhexidine product 10 such that less than 99, less than 95, less than 90, less than 80, less than 70, less than 60, less than 50, less than 40, less than 30, less than 20, less than 10, less than 5, or less than 1, wt. % of the solvent undergoes a phase change from a liquid state to a solid state.

The cooling of the chlorhexidine product 10 may be performed at atmospheric pressure. By way of non-limiting example, the cooling of the chlorhexidine product 10 may be performed at a pressure of at least 1 atm. In other embodiments, the cooling of the chlorhexidine product 10 may be performed at a pressure of from 0.8 to 1.2, of from 0.9 to 1.1, or of from 0.95 to 1.05, atm. Furthermore, once the cooling of the chlorhexidine product 10 is complete the chlorhexidine product 10 may not be exposed to pressures below atmospheric pressure. By way of non-limiting example, after cooling the chlorhexidine product 10 the chlorhexidine product 10 may not be exposed to pressures less than 0.95, less than 0.9, less than 0.8, or less than 0.5, atm. In this manner, the chlorhexidine product 10 is not subjected to lyophilization (also known as freeze-drying).

With continued respect to cooling the chlorhexidine product 10, when a plurality of chlorhexidine articles 14 are included in the package 12, cooling the chlorhexidine product 10 may further comprise cooling the chlorhexidine product 10 such that at least a portion of the solvent in the antiseptic composition of each chlorhexidine article 14 undergoes a phase change from a liquid state to a solid state. In another embodiment, when a plurality of chlorhexidine products 10 are disposed in the shipping container 22, cooling the chlorhexidine product 10 may further comprise cooling the shipping container 22 such that at least a portion of the solvent in the antiseptic composition of each chlorhexidine article 14 in each package 12 undergoes a phase change from a liquid state to a solid state.

Figure 7A:
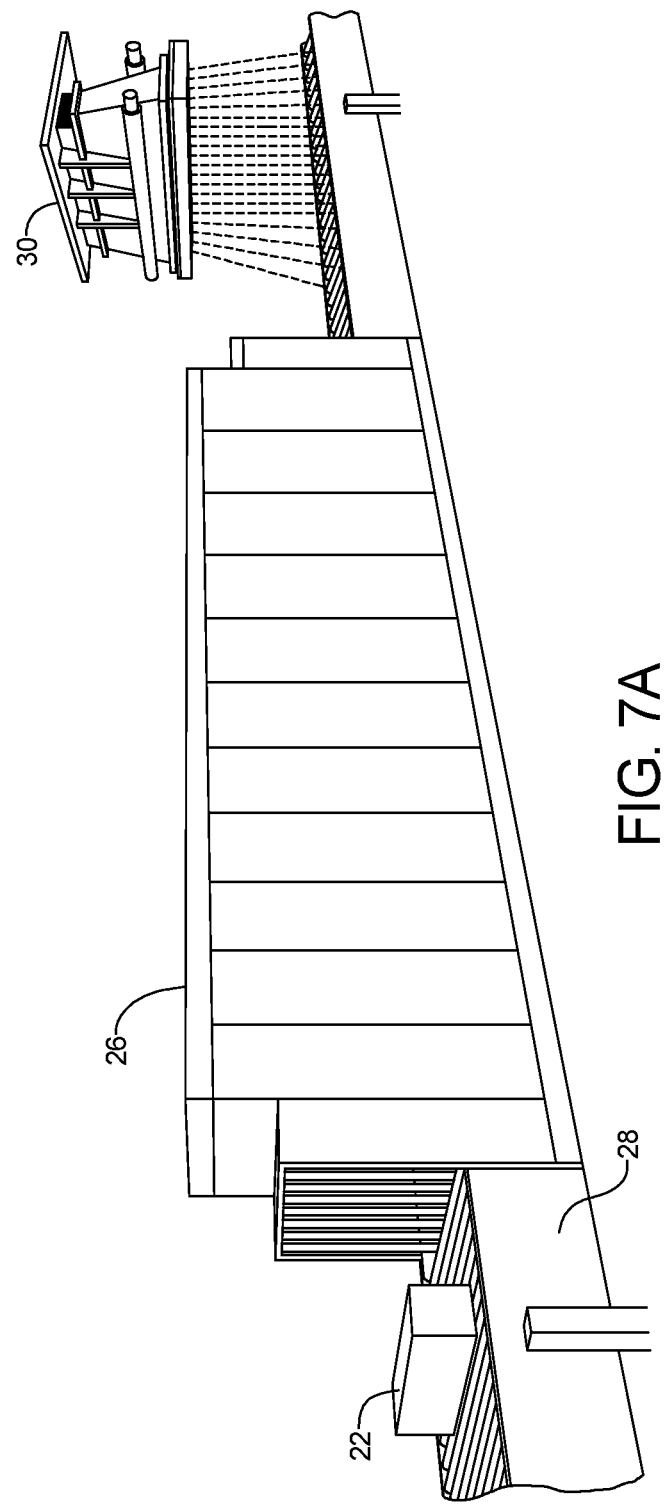
FIG. 7A is a perspective view of a conveyor mechanism including a shipping container, a cooling unit, and a radiation unit.
Figure 7B:
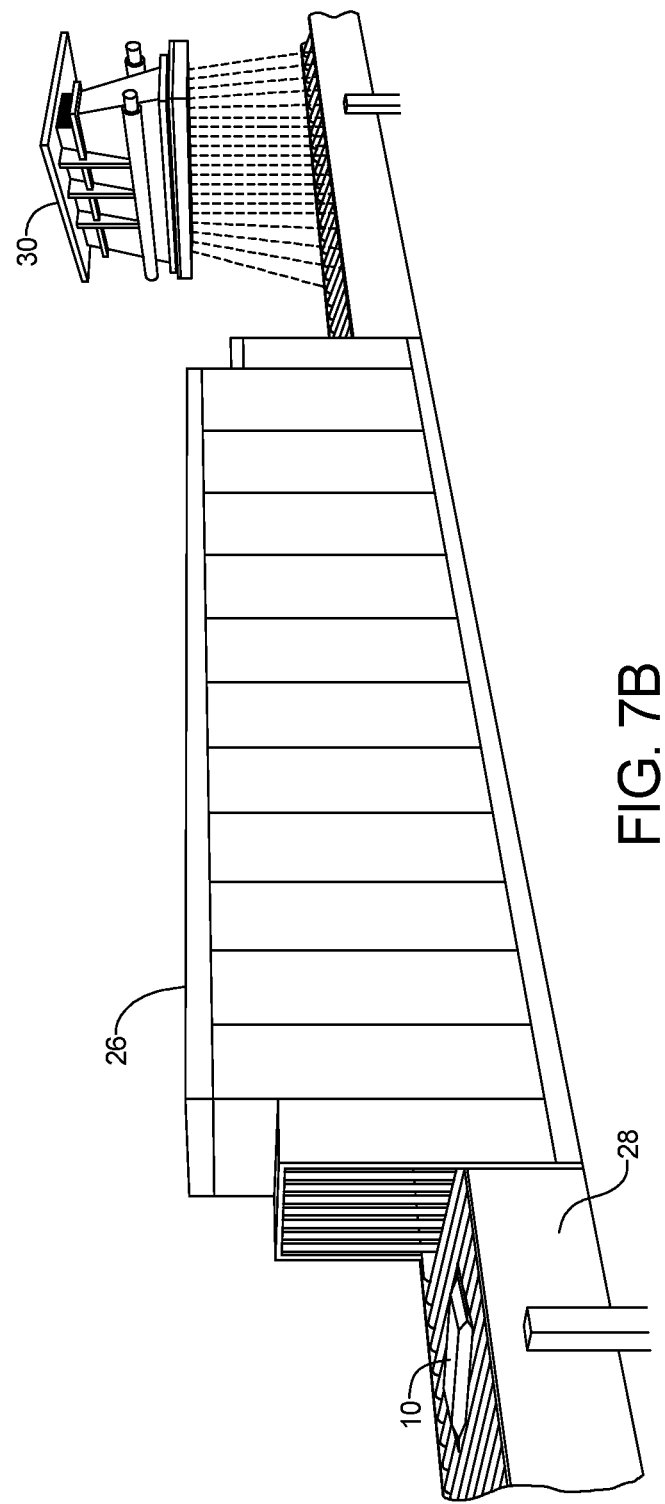
FIG. 7B is a perspective view of the conveyor mechanism of FIG. 7A with a chlorhexidine product in place of the shipping container.

With continued respect to cooling the chlorhexidine product 10, the chlorhexidine product 10 may be cooled by any suitable cooling unit 26. By way of non-limiting example, the cooling unit 26 may be a freezer, a refrigerator, a walk-in freezer, a walk-in cooler, a tunnel blast freezer, or a refrigerated warehouse. Alternatively, the cooling unit 26 may dispense liquid refrigerant such as by way of non-limiting example, liquid nitrogen, liquid nitrous oxide, or liquid carbon dioxide. With reference to FIG. 7A, in one embodiment, the cooling unit 26 is a tunnel blast freezer 26. The tunnel blast freezer 26 may be arranged about a conveyor mechanism 28 to facilitate efficient cooling of the shipping container 22 and the plurality of chlorhexidine products 10 disposed therein. Likewise, as shown in FIG. 7B, the conveyor mechanism may be used to efficiently cool single chlorhexidine products 10 instead of the plurality of chlorhexidine products 10 disposed in the shipping container 22.

In other embodiments, a plurality of shipping containers and the chlorhexidine products 10 disposed therein may be cooled in a freezer, or a walk-in freezer.

The method further comprises sterilizing the chlorhexidine product 10 to form the sterilized chlorhexidine article 14. The chlorhexidine product 10 may be sterilized by any sterilization process such that the sterility of the chlorhexidine article 14 can be verified. In some embodiments, sterilizing the chlorhexidine product 10 comprises irradiating the chlorhexidine product 10 to form a sterilized chlorhexidine article 14.

In other embodiments, sterilizing the chlorhexidine product 10 further comprises heat sterilizing the chlorhexidine product 10. Of course it should be appreciated that the antibacterial agent of the antiseptic composition may not be compatible with heat sterilization. For example, heat sterilization is known to be unsuitable for antiseptic compositions comprising CHG in an amount of greater than 1.0 wt. % based on the total weight of the antiseptic composition because of the degradation of CHG at temperatures required for heat sterilizing. Heat sterilizing may also be incompatible with the applicator 24 and/or package 12 of the chlorhexidine product 10.

In certain embodiments, depending on the chosen antibacterial agent, the method may be free of a heating step that results in the temperature of the chlorhexidine article 14 being raised above 35, 40, 50, 60, or 70, ° C. In other embodiments, the method may be free of a heating step that results in the temperature of the chlorhexidine article 14 being raised above 30° C. In still other embodiments, the method may be free of a heating step that results in the temperature of the chlorhexidine article 14 to be raised such that the chlorhexidine article 14 is considered sterile in accordance with ISO 20857, or ISO 17665. In still other embodiments, the method may be free of a heating step that results in the temperature of the chlorhexidine article 14 being raised to a temperature of from 35 to 150, of from 50 to 150, of from 50 to 130, or of from 75 to 130, ° C.

When the method comprises irradiating the chlorhexidine product 10 to form the sterilized chlorhexidine article 14, irradiating the chlorhexidine product 10 may comprise irradiating the chlorhexidine product 10 with a radiation type selected from the group comprising gamma radiation, electron-beam radiation, x-ray radiation, or combinations thereof. In certain embodiments, the radiation type is electron-beam radiation.

The chlorhexidine product 10 may be irradiated with the radiation type by any suitable radiation unit. With reference to FIGS. 7A and 7B, in the illustrated embodiment, the radiation unit 30 is an irradiator 30. The radiation unit 30 may be arranged in any suitable manner to efficiently irradiate the chlorhexidine product 10. As an example, in the illustrated embodiments, the irradiator 30 is disposed adjacent the conveyor mechanism 28 such that either of the chlorhexidine product 10, or the plurality of chlorhexidine products 10 disposed in the shipping container 22, may be efficiently irradiated. With reference to FIG. 7A, the radiation unit 30 may be disposed adjacent the conveyor mechanism 28 downstream of the cooling unit 26 for efficiently cooling the plurality of chlorhexidine products 10 disposed in the shipping container 22 and subsequently irradiating the plurality of chlorhexidine products 10 disposed in the shipping container 22. Likewise, as shown in FIG. 7B, the conveyor mechanism 28 may also be used for efficiently cooling and irradiating only a single chlorhexidine product 10. It will further be appreciated that in some embodiments, the plurality of chlorhexidine products 10 may be irradiated simultaneously and not disposed in the shipping container 22. Of course, it will be appreciated that cooling the chlorhexidine product 10 may occur separately from irradiating the chlorhexidine product 10. In some embodiments, the irradiator 30 may be arranged about an irradiation platform such that chlorhexidine products can be placed on the irradiation platform and irradiated. Of course other arrangements of the irradiator 30 are contemplated.

When the radiation unit 30 is the irradiator 30, the irradiator 30 may be, by way of non-limiting example, an x-ray generator, a gamma ray irradiator, an electron-beam accelerator, or combinations thereof. Of course, still other irradiators 30 are contemplated.

In some embodiments, when the chlorhexidine product 10 is irradiated with a radiation type, irradiating the chlorhexidine product 10 may further comprise irradiating the chlorhexidine product 10 with a radiation dose of from 5 to 25 kGy to form the sterilized chlorhexidine article 14. In another embodiment, irradiating the chlorhexidine product 10 may further comprise irradiating the chlorhexidine product 10 with a radiation dose of from 1 to 100 kGy. In another embodiment, irradiating the chlorhexidine product 10 may further comprise irradiating the chlorhexidine product 10 with a radiation dose of from 1 to 30 kGy. In other embodiments, irradiating the chlorhexidine product 10 may further comprise irradiating the chlorhexidine product 10 with a radiation dose of from 1 to 55, of from 5 to 30, of from 10 to 25, or of from 10 to 20, of from 8 to 12, or of from 9 to 13, kGy. In still other embodiments, irradiating the chlorhexidine product 10 may further comprise irradiating the chlorhexidine product 10 with a radiation dose of at least 1, at least 5, at least 10, at least 15, at least 20, at least 25, at least 30, at least 50, or at least 100, kGy. In still other embodiments, irradiating the chlorhexidine product 10 may further comprise irradiating the chlorhexidine product 10 with a radiation dose of less than 100, less than 50, less than 30, less than 25, less than 20, less than 15, less than 10, less than 5, or less than 1, kGy. In still other embodiments, irradiating the chlorhexidine product 10 may further comprise irradiating the chlorhexidine product 10 with a radiation dose of 5, 10, 15, 20, 25, or 30, kGy. Of course, still other radiation doses are contemplated.

Irradiating the chlorhexidine product 10 may further comprise irradiating the chlorhexidine product 10 with a plurality of radiation doses. The plurality of radiation doses may be any number of radiation doses suitable to sterilize the chlorhexidine product 10. By way of non-limiting example, the plurality of doses may be of from 2 to 5, of from 2 to 4, or of from 2 to 3, radiation doses. The chlorhexidine product 10 may be subjected to the plurality of radiation doses within 7, within 6, within 5, within 3, within 3, within 2, or within 1, days. In other embodiments, the chlorhexidine product 10 may be subjected to the plurality of radiation doses within 20, within 15, within 10, or within 5, hours. In one embodiment, the chlorhexidine product 10 may be subjected to one of the plurality of radiation doses immediately after another of the plurality of radiation doses. Each of the plurality of radiation doses may be a radiation dose of from 5 to 25 kGy, or any of the radiation dose ranges described herein.

With continued respect to irradiating the chlorhexidine product 10, irradiating the chlorhexidine product 10 may further comprise irradiating the chlorhexidine product 10 while at least a portion of the solvent is in the solid state to form the sterilized chlorhexidine article 14. In some embodiments, irradiating the chlorhexidine product 10 may further comprise irradiating the chlorhexidine product 10 while at least 50 wt. % of the solvent is in the solid state. In another embodiment, irradiating the chlorhexidine product 10 may further comprise irradiating the chlorhexidine product 10 while at least 75 wt. % of the solvent is in the solid state. In other embodiments, irradiating the chlorhexidine product 10 may further comprise irradiating the chlorhexidine product 10 while at least 1, at least 5, at least 10, at least 15, at least 20, at least 30, at least 40, at least 60, at least 70, at least 80, at least 90, at least 95, or at least 99, wt. % of the solvent is in the solid state. In certain embodiments, irradiating the chlorhexidine product 10 may further comprise irradiating the chlorhexidine product 10 while all of the solvent is in the solid state. Alternatively, irradiating the chlorhexidine product 10 may further comprise irradiating the chlorhexidine product 10 while none of the solvent is in the solid state irradiating the chlorhexidine product 10 may further comprise irradiating the chlorhexidine product 10 while less than 99, less than 95, less than 90, less than 80, less than 70, less than 60, less than 50, less than 40, less than 30, less than 20, less than 10, less than 5, or less than 1, wt. % of the solvent is in the solid state.

In some embodiments, the amount of solvent in the solid state when the chlorhexidine product 10 is irradiated is the same as the amount of solvent that undergoes a phase change from the liquid state to the solid state when the chlorhexidine product 10 is cooled. For example, with reference to FIGS. 7A and 7B, when the radiation unit 30 is arranged downstream of the cooling unit 26 on the conveyor mechanism 28, the amount of solvent in the solid state when the chlorhexidine products are irradiated is the same, substantially the same, or slightly less than, the amount of solvent that undergoes a phase change from the liquid state to the solid state during cooling of the chlorhexidine products 10. Alternatively, the radiation unit may be arranged separately from the cooling unit. When the radiation unit is arranged separately from the cooling unit, the radiation unit may be arranged in a cooled environment to ensure the amount of solvent in the solid state when the chlorhexidine products 10 are irradiated is the same, substantially the same, or slightly less than, the amount of solvent that undergoes a phase change from the liquid state to the solid state during cooling of the chlorhexidine products 10. Of course, the radiation unit may be arranged in a room temperature environment.

In other embodiments, the amount of solvent in the solid state when the chlorhexidine product 10 is irradiated is different to the amount of solvent that undergoes a phase change from the liquid state to the solid state when the chlorhexidine product 10 is cooled.

In some embodiments, the sterilized antibacterial agent in the sterilized antiseptic composition has a purity of at least 90% after irradiating the chlorhexidine product 10 to form the sterilized chlorhexidine article 14. In the context of this disclosure, the purity of the sterilized antibacterial agent is the amount of sterilized antibacterial agent in the sterilized antiseptic composition after sterilizing the chlorhexidine product 10 divided by the sum of the amount of sterilized antibacterial agent and degradation impurities in the sterilized antiseptic composition after sterilizing the chlorhexidine product 10, expressed as a percentage. The purity may be expressed in the following formula:

$$\text{purity} = \frac{\text{amount of sterilized antibacterial agent in the sterilized antiseptic composition}}{(\text{amount of sterilized antibacterial agent in the sterilized antiseptic composition} + \text{amount of degradation impurities in the sterilized antiseptic composition})} \times 100.$$

For example, a purity of 98% indicates that the sterilized antiseptic composition comprises 98 parts of the sterilized antibacterial agent in the sterilized antiseptic composition and 2 parts of the degradation impurities in the sterilized antiseptic composition. In another embodiment, the sterilized antibacterial agent in the sterilized antiseptic composition has a purity of at least 50%. In other embodiments, the sterilized antibacterial agent in the sterilized antiseptic composition has a purity of at least 60%, of at least 70%, of at least 80%, of at least 90%, of at least 92.5%, of at least 95%, of at least 97.5%, of at least 99%, of at least 99.5%, or of at least 99.9%. In certain embodiments, the sterilized antibacterial agent in the sterilized antiseptic composition has a purity of 100%. In other words, the sterilized antiseptic composition does not comprise any degradation impurities. In still other embodiments, the sterilized antibacterial agent in the antiseptic composition has purity of from 85 to 99.5%, of from 87.5 to 99.5%, or of from 87.5 to 97.5%. Of course, still other purities of the sterilized antibacterial agent of the sterilized antiseptic composition are contemplated.

In some embodiments, the sterilized antibacterial agent in the sterilized antiseptic composition is present in an amount at least 90% of the amount of the antibacterial agent in the antiseptic composition before sterilizing the chlorhexidine product 10. In another embodiment, the sterilized antibacterial agent in the sterilized antiseptic composition is present in an amount at least 85% of the amount of the antibacterial agent in the antiseptic composition before sterilizing the chlorhexidine product 10. In still other embodiments, the sterilized antibacterial agent in the sterilized antiseptic composition is present in an amount at least 50%, at least 60%, at least 70%, at least 80%, at least 92.5%, at least 95%, at least 97.5%, at least 99%, at least 99.5%, at least 99.9%, of the amount of the antibacterial agent in the antiseptic composition before sterilizing the chlorhexidine product 10. In certain embodiments, the sterilized antibacterial agent in the sterilized antiseptic composition is present in an amount equal to the amount of the antibacterial agent in the antiseptic composition before sterilizing the chlorhexidine product 10. In still other embodiments, the sterilized antibacterial agent in the sterilized antiseptic composition is present in an amount of from 85 to 99.5%, of from 87.5 to 99.5%, or of from 87.5 to 97.5%, of the antibacterial agent in the antiseptic composition before sterilizing the chlorhexidine product 10. Of course, it is contemplated the sterilized antibacterial agent in the sterilized antiseptic composition is present in still other amounts.

In some embodiments, the antibacterial agent may be included in the antiseptic composition in an amount greater than the desired amount of the sterilized antibacterial agent in the sterilized antiseptic composition. In this manner, if the amount of antibacterial agent decreases during sterilization, there may still be a therapeutically effective amount of the sterilized antibacterial agent included in the sterilized antiseptic composition. In one embodiment, the antibacterial agent may be included in an amount less than 35% greater than the desired amount of the sterilized antibacterial agent included in the sterilized antiseptic composition. In another embodiment, the antibacterial agent may be included in the antiseptic composition an amount of from 15 to 25% greater than the desired amount of the sterilized antibacterial agent included in the sterilized antiseptic composition. In still other embodiments, the antibacterial agent may be included in the antiseptic composition an amount less than 5%, less than 10%, less than 15%, less than 20%, less than 25%, less than 30%, less than 40%, less than 50%, less than 60%, less than 70%, less than 80%, less than 90%, less than 100%, less than 200%, or less than 500%, greater than the desired amount of the sterilized antibacterial agent included in the sterilized antiseptic composition. In still other embodiments, the antibacterial agent may be included in the antiseptic composition an amount more than 5%, more than 10%, more than 15%, more than 20%, more than 25%, more than 30%, more than 40%, more than 50%, more than 60%, more than 70%, more than 80%, more than 90%, more than 100%, more than 200%, or more than 500%, greater than the desired amount of the sterilized antibacterial agent included in the sterilized antiseptic composition. Of course, the antibacterial agent may be included in the antiseptic composition in still other amounts greater than the desired amount of the sterilized antibacterial agent in the sterilized antiseptic composition.

When the antibacterial agent is included in the antiseptic composition amounts greater than the desired amount of the sterilized antibacterial agent in the sterilized antiseptic composition, the sterilized antibacterial agent may be included in the sterilized antiseptic composition in an amount of from 0.1 to 10 wt. % based on the total weight of the sterilized antiseptic composition. In another embodiment, the sterilized antibacterial agent may be included in an amount of from 1.5 to 5.0 wt. % based on the total weight of the sterilized antiseptic composition. In other embodiments, the sterilized antibacterial agent may be included in an amount from 0.5 to 10, of from 1.0 to 10, of from 1.5 to 10, of from 2.0, to 10, of from 2.5 to 10, of from 3.0 to 10, of from 3.5 to 10, of from 4.0 to 10, of from 4.5 to 10, of from 5.0 to 10, of from 5.5 to 10, of from 6.0 to 10, of from 6.5 to 10, of from 7.0 to 10, of from 7.5 to 10, of from 8.0 to 10, of from 8.5 to 10, of from 9.0 to 10, or of from 9.5 to 10 wt. % based on the total weight of the sterilized antiseptic composition. In still other embodiments, the sterilized antibacterial agent may be included in the sterilized antiseptic composition in an amount of from 0.1 to 9.5, of from 0.1 to 9.0, of from 0.1 to 8.5, of from 0.1 to 8.0, of from 0.1 to 7.5, of from 0.1 to 7.0, of from 0.1 to 6.5, of from 0.1 to 6.0, of from 0.1 to 5.5, of from 0.1 to 5.0, of from 0.1 to 4.5, of from 0.1 to 4.0, of from 0.1 to 3.5, of from 0.1 to 3.0, of from 0.1 to 2.5, of from 0.1 to 2.0, of from 0.1 to 1.5, of from 0.1 to 1.0, or of from 0.1 to 0.5, wt. % based on the total weight of the sterilized antiseptic composition. In still other embodiments, the sterilized antibacterial agent may be included in the sterilized antiseptic composition in an amount of from 0.5 to 8.0, of from 1.0 to 6.0, of from 1.5 to 5.0, of from 1.8 to 4.5, of from 1.8 to 3.5, or of from 1.8 to 2.5, wt. % based on the total weight of the sterilized antiseptic composition. Of course, the sterilized antibacterial agent may be included in the sterilized antiseptic composition in still other amounts.

In one embodiment, the method of sterilizing a chlorhexidine article comprises providing an applicator. The method further comprises, providing an antiseptic composition comprising water in an amount of from 50 wt. % based on the total weight of the antiseptic composition and CHG in an amount of from 1.5 to 5.0 wt. % based on the total weight of the antiseptic composition. The method further comprises, impregnating the antiseptic composition in the applicator to form the chlorhexidine article. The method further comprises sealing the chlorhexidine article inside the package to form the chlorhexidine product. The method further comprises cooling the chlorhexidine product such that at least a portion of the water of the antiseptic composition undergoes a phase change from the liquid state to the solid state. The method further comprises irradiating the chlorhexidine product while at least a portion of the water is in the solid state to form the sterilized chlorhexidine article.

In another embodiment, the method of sterilizing a chlorhexidine article comprises providing the chlorhexidine product. The method also comprises cooling the chlorhexidine product such that at a least a portion of the solvent of the antiseptic composition undergoes a phase change from a liquid state to a solid state. The method further comprises irradiating the chlorhexidine product while at least a portion of the solvent is in the solid state to form a sterilized chlorhexidine article.

One or more of the values described above may vary by ±5%, ±10%, ±15%, ±20%, ±25%, etc. so long as the variance remains within the scope of the disclosure. Each member may be relied upon individually and or in combination and provides adequate support for specific embodiments within the scope of the appended claims. The subject matter of all combinations of independent and dependent claims, both singly and multiply dependent, is herein expressly contemplated. The disclosure is illustrative including words of description rather than of limitation. Many modifications and variations of the present disclosure are possible in light of the above teachings, and the disclosure may be practiced otherwise than as specifically described herein.

All combinations of the aforementioned embodiments throughout the entire disclosure are hereby expressly contemplated in one or more non-limiting embodiments even if such a disclosure is not described verbatim in a single paragraph or section above. In other words, an expressly contemplated embodiment may include any one or more elements described above selected and combined from any portion of the disclosure It is also to be understood that any ranges and subranges relied upon in describing various embodiments of the present disclosure independently and collectively fall within the scope of the appended claims, and are understood to describe and contemplate all ranges including whole and/or fractional values therein, even if such values are not expressly written herein. One of skill in the art readily recognizes that the enumerated ranges and subranges sufficiently describe and enable various embodiments of the present disclosure, and such ranges and subranges may be further delineated into relevant halves, thirds, quarters, fifths, and so on. As just one example, a range "of from 0.1 to 0.9" may be further delineated into a lower third, i.e. from 0.1 to 0.3, a middle third, i.e. from 0.4 to 0.6, and an upper third, i.e. from 0.7 to 0.9, which individually and collectively are within the scope of the appended claims, and may be relied upon individually and/or collectively and provide adequate support for specific embodiments within the scope of the appended claims. In addition, with respect to the language which defines or modifies a range, such as "at least," "greater than," "less than," "no more than," and the like, it is to be understood that such language includes subranges and/or an upper or lower limit. As another example, a range of "at least 10" inherently includes a subrange of from at least 10 to 35, a subrange of from at least 10 to 25, a subrange of from 25 to 35, and so on, and each subrange may be relied upon individually and/or collectively and provides adequate support for specific embodiments within the scope of the appended claims. Finally, an individual number within a disclosed range may be relied upon and provides adequate support for specific embodiments within the scope of the appended claims. For example, a range "of from 1 to 9" includes various individual integers, such as 3, as well as individual numbers including a decimal point (or fraction), such as 4.1, which may be relied upon and provide adequate support for specific embodiments within the scope of the appended claims.

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A sterilized chlorhexidine product for topical disinfection, said sterilized chlorhexidine product comprising:
a sterilized chlorhexidine gluconate composition;
an applicator for facilitating application of the sterilized chlorhexidine composition; and
a barrier configured to be compromised to impregnate the applicator with the sterilized chlorhexidine gluconate composition;
wherein the sterilized chlorhexidine gluconate composition comprises chlorhexidine gluconate and alcohol.

2. The sterilized chlorhexidine product of claim 1, comprising the sterilized chlorhexidine gluconate composition in an amount between 0.1 and 100 mL.

3. The sterilized chlorhexidine product of claim 1, wherein the sterilized chlorhexidine gluconate composition comprises chlorhexidine gluconate in an amount of from 1.5 to 5.0 wt. % based on the total weight of said sterilized antiseptic composition and the alcohol in an amount of at least 50 wt. % based on a total weight of said sterilized antiseptic composition.

4. The sterilized chlorhexidine product of claim 3, wherein the sterilized chlorhexidine gluconate composition comprises chlorhexidine gluconate in an amount of 2.0 wt. % based on the total weight of said sterilized antiseptic composition and the alcohol in an amount of 70 wt. % based on a total weight of said sterilized antiseptic composition.

5. The sterilized chlorhexidine product of claim 1, wherein the alcohol is isopropyl alcohol.

6. The sterilized chlorhexidine product of claim 1, wherein the sterilized chlorhexidine gluconate composition further comprises water.

7. The sterilized chlorhexidine product of claim 1, wherein the sterilized chlorhexidine gluconate composition further comprises one or more additives selected from the group consisting of a sterilized surfactant, a sterilized pH adjuster, a sterilized odorant, a sterilized colorant, a sterilized stabilizer, a sterilized skin protectant, a sterilized preservative, or combinations thereof.

8. The sterilized chlorhexidine product of claim 7, wherein the additive is a colorant.

9. The sterilized chlorhexidine product of claim 7, wherein the additive is a skin protectant.

10. The sterilized chlorhexidine product of claim 1, wherein said sterilized chlorhexidine article has a sterility assurance level of from 10-3 to 10-9.

11. The sterilized chlorhexidine product of claim 1, wherein the applicator comprises a foam.

12. A method of using a sterilized chlorhexidine article, said method comprising:
providing a sterilized chlorhexidine article, the sterilized chlorhexidine article comprising:
a sterilized chlorhexidine gluconate composition comprising chlorhexidine gluconate and alcohol;
an applicator for facilitating application of the sterilized chlorhexidine; and
a barrier between the sterilized chlorhexidine gluconate composition and the applicator;
compromising the barrier to impregnate the applicator with the sterilized chlorhexidine gluconate composition; and
applying the sterilized chlorhexidine gluconate composition to a patient's skin using the applicator.

13. The method of claim 12, wherein the applicator is impregnated with 0.1 to 100 mL of the sterilized chlorhexidine gluconate composition.

14. The method of claim 12, wherein the sterilized chlorhexidine gluconate composition comprises chlorhexidine gluconate in an amount of from 1.5 to 5.0 wt. % based on the total weight of said sterilized antiseptic composition and the alcohol in an amount of at least 50 wt. % based on a total weight of said sterilized antiseptic composition.

15. The method of claim 12, wherein the alcohol is isopropyl alcohol.

16. The method of claim 12, wherein the sterilized chlorhexidine gluconate composition further comprises water.

17. The method of claim 12, wherein the sterilized chlorhexidine gluconate composition further comprises one or more additives selected from the group consisting of a sterilized surfactant, a sterilized pH adjuster, a sterilized odorant, a sterilized colorant, a sterilized stabilizer, a sterilized skin protectant, a sterilized preservative, or combinations thereof.

18. The method of claim 17, wherein the additive is a colorant or a skin protectant.

19. The method of claim 12, wherein said sterilized chlorhexidine article has a sterility assurance level of from $10^{-3}$ to $10^{-9}$.

* * * * *

(12) INTER PARTES REVIEW CERTIFICATE (4182nd)
United States Patent
Allen et al.

(10) Number: US 10,688,067 K1
(45) Certificate Issued: Nov. 7, 2025

(54) STERILIZED CHLORHEXIDINE ARTICLE AND METHOD OF STERILIZING A CHLORHEXIDINE ARTICLE

(71) Applicants: Jennifer M. Allen; Christopher J. Grannis; Syed M. Hasan; Timothy P. Manthei; Niles R. Manwill

(72) Inventors: Jennifer M. Allen; Christopher J. Grannis; Syed M. Hasan; Timothy P. Manthei; Niles R. Manwill

(73) Assignee: SAGE PRODUCTS, LLC

Trial Number:

IPR2021-01202 filed Jun. 30, 2021

Inter Partes Review Certificate for:

Patent No.: 10,688,067
Issued: Jun. 23, 2020
Appl. No.: 16/557,160
Filed: Aug. 30, 2019

The results of IPR2021-01202 are reflected in this inter partes review certificate under 35 U.S.C. 318(b).

INTER PARTES REVIEW CERTIFICATE
U.S. Patent 10,688,067 K1
Trial No. IPR2021-01202
Certificate Issued Nov. 7, 2025

AS A RESULT OF THE INTER PARTES REVIEW PROCEEDING, IT HAS BEEN DETERMINED THAT:

Claims 1-3, 5-8 and 10-19 are cancelled.

* * * * *